US012311084B2

United States Patent
Ahn et al.

(10) Patent No.: US 12,311,084 B2
(45) Date of Patent: May 27, 2025

(54) PLASMA STERILIZATION MODULE AND AIR PURIFIER HAVING SAME

(71) Applicant: LG ELECTRONICS INC., Seoul (KR)

(72) Inventors: Jihye Ahn, Seoul (KR); Sujin Lee, Seoul (KR); Chulwoo Park, Seoul (KR); Jaesoo Jang, Seoul (KR); Ilna Son, Seoul (KR); Bongjo Sung, Seoul (KR)

(73) Assignee: LG ELECTRONICS INC., Sseoul (KR)

( * ) Notice: Subject to any disclaimer, the term of this patent is extended or adjusted under 35 U.S.C. 154(b) by 877 days.

(21) Appl. No.: 17/294,733

(22) PCT Filed: Nov. 29, 2019

(86) PCT No.: PCT/KR2019/016791
§ 371 (c)(1),
(2) Date: May 18, 2021

(87) PCT Pub. No.: WO2020/111894
PCT Pub. Date: Jun. 4, 2020

(65) Prior Publication Data
US 2022/0016307 A1 Jan. 20, 2022

(30) Foreign Application Priority Data

Nov. 29, 2018 (KR) .................. 10-2018-0151048
Nov. 29, 2018 (KR) .................. 10-2018-0151049

(51) Int. Cl.
*A61L 9/22* (2006.01)
(52) U.S. Cl.
CPC .......... *A61L 9/22* (2013.01); *A61L 2209/134* (2013.01)

(58) Field of Classification Search
CPC .. A61L 9/22; A61L 2209/134; A61L 2209/16; H05H 2245/15; H05H 1/48
See application file for complete search history.

(56) References Cited

U.S. PATENT DOCUMENTS

| 8,529,830 B2 | 9/2013 | Zhou et al. | |
|---|---|---|---|
| 2003/0108460 A1* | 6/2003 | Andreev | ................ A61L 2/202 422/186.07 |

(Continued)

FOREIGN PATENT DOCUMENTS

| JP | 2004-351310 | 12/2004 |
|---|---|---|
| KR | 10-1999-0001066 | 1/1999 |

(Continued)

OTHER PUBLICATIONS

International Search Report dated May 21, 2020 issued in Application No. PCT/KR2019/016791.

(Continued)

*Primary Examiner* — Sean E Conley
*Assistant Examiner* — Brendan A Hensel
(74) *Attorney, Agent, or Firm* — KED & ASSOCIATES

(57) ABSTRACT

The present invention relates to a plasma sterilization module, comprising: a housing which is disposed on a flow path through which air flows, and having a first surface through which the air is introduced and a second surface, opposite to the first surface, through which the introduced air is discharged; a discharge electrode disposed in the housing; and a ground electrode disposed in the housing and spaced apart from the discharge electrode, wherein the discharge electrode is applied with a high voltage to generate a plasma discharge toward the ground electrode between the first surface and the second surface, and the discharge electrode and the ground electrode are disposed so as to allow air introduced into the first surface to directly pass through an (Continued)

area wherein the plasma discharge occurs, and be discharged to the second surface, thereby sterilizing microbes in the air.

17 Claims, 22 Drawing Sheets

(56) References Cited

U.S. PATENT DOCUMENTS

| | | | |
|---|---|---|---|
| 2006/0024219 A1* | 2/2006 | Park | A01N 59/00 422/186.04 |
| 2006/0227493 A1 | 10/2006 | Kim et al. | |
| 2016/0074805 A1* | 3/2016 | Liu | B01J 19/2425 422/168 |

FOREIGN PATENT DOCUMENTS

| | | |
|---|---|---|
| KR | 10-0495345 | 6/2005 |
| KR | 10-2006-0085647 | 7/2006 |
| KR | 10-0635341 | 10/2006 |
| KR | 10-2007-0094026 | 9/2007 |
| KR | 10-2013-0068103 | 6/2013 |
| KR | 20-0479602 | 2/2016 |
| KR | 10-2017-0032698 | 3/2017 |

OTHER PUBLICATIONS

German Office Action dated Apr. 18, 2023 issued in Application No. 11 2019 005 969.6.

* cited by examiner

FIG. 10A
FIG. 10B
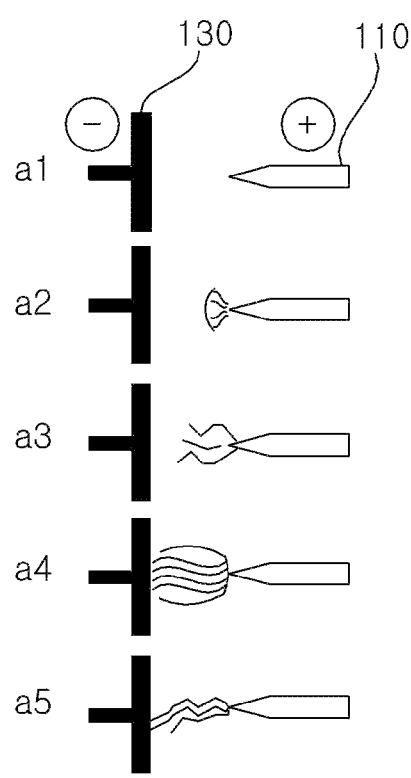
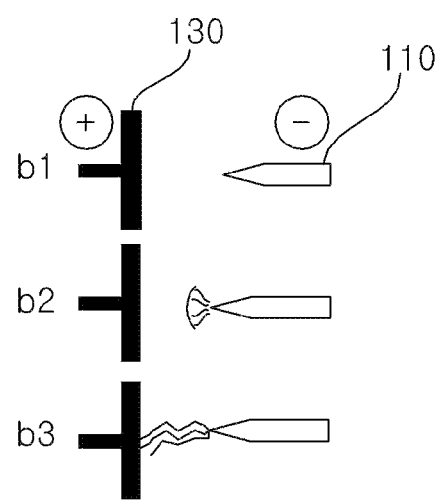

PLASMA STERILIZATION MODULE AND AIR PURIFIER HAVING SAME

CROSS-REFERENCE TO RELATED PATENT APPLICATIONS

This application is a U.S. National Stage Application under 35 U.S.C. § 371 of PCT Application No. PCT/KR2019/016791, filed Nov. 29, 2019, which claims priority to Korean Patent Application Nos. 10-2018-0151048 and 10-2018-0151049, both filed Nov. 29, 2018, whose entire disclosures are hereby incorporated by reference.

BACKGROUND OF THE DISCLOSURE

Field of the Disclosure

The present disclosure relates to a plasma sterilization module and an air purifier having the plasma sterilization module and, more particularly, to a plasma sterilization module intended to sterilize contaminated air using plasma discharge and an air purifier having the plasma sterilization module.

Related Art

An air purifier refers to a device that purifies contaminated air to change it into fresh air. The air purifier is operated to suck the contaminated air by a fan, collect fine dust or bacteria by a filter, and remove bad smells such as a body odor or a cigarette odor.

Such an air purifier is required to effectively remove contaminants from the air. Further, it is required to increase an air cleaning capacity while occupying a small space when the air purifier is placed indoors.

To this end, methods for performing sterilization treatment using a plasma discharge have been proposed.

For example, the related art 1 (Korean Patent Laid-Open Publication No. 10-2007-0094026) relates to an air conditioner configured such that a discharge unit and a heat exchanger are installed in an air passage. The discharge unit is a streamer discharge which is a kind of the plasma discharge, and improves the decomposition efficiency of components to be treated.

In addition, the related art 2 (Korean Patent Laid-Open Publication No. 10-2006-0085647 proposes an air conditioner using a streamer discharge.

However, the related art is problematic in that sterilization treatment is performed by generating radicals through the streamer discharge and then diffusing the radicals, instead of making air pass through an area where the streamer discharge occurs, so that it is difficult to improve sterilization performance.

Furthermore, in order to improve the sterilization performance, a discharge intensity should be increased or the number of discharge units should be increased. However, this is problematic in that ozone having the concentration of 30 ppb (parts per billion) is generated according to the air clean standard.

Furthermore, in order to improve the sterilization performance by radicals, a catalytic means is required. The catalytic means is disposed on an outlet side to be perpendicular to the air flow path. Thus, this interferes with an air flow, thus increasing a differential pressure. The conventional discharge unit is problematic in that it interferes with the air flow, thus causing an increase in differential pressure.

Furthermore, the related art is problematic in that the shape of the discharge unit is limited, and thereby it is difficult to apply the discharge unit to various shapes of air purifiers.

Meanwhile, the related art 3 (Korean Patent Laid-Open Publication No. 10-2017-0032698) proposes a device for collecting and deactivating airborne microbes. The collecting and deactivating of the related art 3 includes a first high-voltage electrode and a first counter electrode which charge microbes to collect the microbes, a filter which collects the charged airborne microbes, and a second high-voltage electrode and a second counter electrode which charge microbes to collect the microbes which deactivate the microbes collected by the filter. The filter is provided between the second high-voltage electrode and the second counter electrode, a discharge is performed only in a first high-voltage application electrode when the airborne microbes are collected, and a discharge is performed only in a second high-voltage application electrode when the collected microbes are deactivated.

The first high-voltage application electrode is configured such that the airborne microbes do not directly pass through the discharge area, so that the microbes are merely indirectly charged, and thereby it is difficult to attain sterilization performance. Consequently, the sterilization treatment is performed by the second high-voltage application electrode.

The related art 3 is problematic in that the microbes collected by the filter are sterilized, but surviving microbes present in the filter may be multiplied in the filter and then may be re-scattered.

Furthermore, the related art 3 is problematic in that it should have the filter, so that this may cause an increase in differential pressure may increase as in the catalytic means of the related art 1 and 2.

SUMMARY

The present disclosure provides a plasma sterilization module, in which a plasma discharge area is formed in a flow path through which air flows, and airborne microbes are sterilized by charges, thus improving sterilization performance.

The present disclosure provides a plasma sterilization module, in which microbes are sterilized and charged by a glow discharge, and microbes are sterilized by a streamer discharge, thus significantly improving sterilization performance.

The present disclosure provides a plasma sterilization module, in which microbes are sterilized by charges to improve sterilization performance, and the concentration of ozone generated by a plasma discharge is reduced, thus meeting air clean standards for ozone.

The present disclosure provides a plasma sterilization module, in which microbes are sterilized by charges, so that a separate catalytic means and microbe collecting filter causing an increase in differential pressure are not required.

The present disclosure provides a plasma sterilization module, which is installed on a flow path through which air flows, and is formed to minimize flow-path resistance, thus reducing a pressure difference between an upstream side and a downstream side.

The present disclosure provides a plasma sterilization module, which increases the degree of freedom in shape, so that this may be applied to various shapes of air purifiers and air conditioners, and this may apply a plurality of modules to an air purifier and an air conditioner.

Objects of the present disclosure are not limited to the above-mentioned objects, and other objects that are not mentioned will be clearly understood by those skilled in the art from the following description.

In an aspect, a plasma sterilization module includes a housing disposed on a flow path through which air flows, and having a first surface into which the air is introduced and a second surface which is opposite to the first surface and through which the introduced air is discharged; a discharge electrode disposed in the housing; and a ground electrode disposed in the housing and spaced apart from the discharge electrode, A high voltage is applied to the discharge electrode to generate a plasma discharge toward the ground electrode between the first surface and the second surface, and the discharge electrode and the ground electrode are disposed so as to allow air introduced into the first surface to pass through an area in which the plasma discharge occurs, and be discharged to the second surface The discharge electrode and the ground electrode may be disposed such that the area in which the plasma discharge occurs intersects with the flow path of the air.

The discharge electrode and the ground electrode may be disposed such that the area in which the plasma discharge occurs is perpendicular to a direction in which the air flows.

A circumferential surface of the housing forming the opened first and second surfaces may be parallel to the flow path through which the air flows.

The discharge electrode and the ground electrode may be disposed to be parallel to the circumferential surface of the housing.

The discharge electrode may include a plurality of discharge electrode plates spaced apart from each other; and a plurality of discharge needles provided on the plurality of discharge electrode plates, respectively, to generate the plasma discharge, and the ground electrode may include at least one counter electrode plate disposed between the plurality of discharge electrode plates which are spaced apart from each other.

The discharge electrode plate and the counter electrode plate may be disposed to be parallel to the circumferential surface of the housing forming the first and second surfaces.

The discharge needle may be provided with two tips which are symmetrical to each other.

The ground electrode may include a plurality of counter electrode plates.

The discharge electrode may include a discharge-electrode support portion which connects the plurality of discharge electrode plates to each other and is disposed to be supported on the housing, and the ground electrode may include a ground-electrode support portion which is connected to the counter electrode plate and is disposed to be supported on the housing.

The plurality of discharge electrode plates and the plurality of counter electrode plates may be disposed to have the same distance between the discharge electrode plate and the counter electrode plate which are adjacent to each other.

The plurality of discharge needles located between the plurality of counter electrode plates may protrude towards the counter electrode plates, and protrude towards the counter electrode plates which are disposed inside and outside the discharge electrode plates alternately having the plurality of discharge needles.

A discharge electrode plate disposed on an outermost side, among the plurality of discharge electrode plates, may be disposed outside a counter electrode plate disposed on an outermost side, among the plurality of counter electrode plates, and the plurality of discharge needles provided on the discharge electrode plate disposed on the outermost side may protrude towards the counter electrode plate disposed on the outermost side.

The housing may be formed to have a shape of a cylinder with the opened first and second surfaces, the discharge electrode may be provided with a plurality of ring-shaped discharge electrode plates forming concentric circles around a central axis of the housing, and the ground electrode may be provided with a plurality of ring-shaped counter electrode plates forming concentric circles around the central axis of the housing.

The housing may include a rim surface which protrudes inwards from an inner circumferential surface and is located in either of the first surface or the second surface, a hub ring located in the center of either of the first surface or the second surface, and radial spokes connecting the rim surface and the hub ring.

The discharge electrode may include a voltage application portion supplied with a high voltage and seated on the hub ring, the discharge electrode plate located on the outermost side, among the plurality of discharge electrode plates, may be seated on the rim surface, and the discharge-electrode support portions may connect the voltage application portion and the plurality of discharge electrode plates, and may be seated on the spokes.

The housing may have guide grooves formed in a remaining one of the first surface or the second surface, the guide grooves being recessed outwards from the inner circumference, and the ground-electrode support portions may connect the plurality of counter electrode plates, and outer ends thereof may be seated on the guide grooves.

The housing may be shaped such that its circumferential surface has a rectangular section, and the discharge electrode plate and the counter electrode plate may be disposed to be parallel to a pair of facing portions of the circumferential surface of the housing.

The discharge electrode may be formed of stainless steel, and an outer surface of at least a portion thereof may be plated with nickel-cobalt alloy.

The discharge electrode may be supplied with a high positive voltage to generate the streamer discharge towards the ground electrode.

The plasma sterilization module may include a plurality of discharge modules each having the housing, the discharge electrode, and the ground electrode, the plurality of discharge modules may be disposed on the flow path through which the air flows to be parallel to each other, and may be disposed such that the second surface of the discharge module disposed on the upstream side is opposite to the first surface of the discharge module disposed on the downstream side.

The discharge electrode include a first discharge electrode which is supplied with a high voltage to generate a plasma discharge towards the ground electrode, and a second discharge electrode which is disposed downstream of the air flow path compared to the first discharge electrode and is supplied with a high voltage to generate a plasma discharge towards the ground electrode.

The first and second discharge electrodes and the ground electrode may be disposed such that the area in which the plasma discharge occurs intersects with the air flow path.

The first discharge electrode may be supplied with a high negative voltage to generate the glow discharge towards the ground electrode, and the second discharge electrode may be supplied with a high positive voltage to generate the streamer discharge towards the ground electrode.

The ground electrode may include a first ground electrode disposed to be opposite to the first discharge electrode, and a second ground electrode disposed on the downstream side of the air flow path compared to the first ground electrode and disposed to be opposite to the second discharge electrode.

The housing may include a first housing configured to accommodate the first discharge electrode and the first ground electrode; and a second housing configured to accommodate the second discharge electrode and the second ground electrode.

The plasma sterilization module may include a first discharge module having the first discharge electrode, the first ground electrode, and the first housing; and a second discharge module having the second discharge electrode, the second ground electrode, and the second housing.

The first discharge module and the second discharge module may be formed to have the same shape.

The first discharge module may apply a high negative voltage to the first discharge electrode to generate a glow discharge towards the first ground electrode, and the second discharge module may be disposed on the downstream side of the air flow path compared to the first discharge module, and may apply a high positive voltage to the second discharge electrode to generate a streamer discharge towards the second ground electrode.

The first discharge module and the second discharge module may be disposed such that they are spaced apart from each other in the direction where the air flows, and the second surface of the first housing and the first surface of the second housing are opposite to each other.

The first discharge electrode may include a plurality of first discharge electrode plates which are disposed to be spaced apart from each other, and a plurality of first discharge needles which are provided in each of the first discharge electrode plates and generate the plasma discharge. The first ground electrode may include a plurality of first counter electrode plates disposed between the plurality of first discharge electrode plates which are spaced apart from each other.

The second discharge electrode may include a plurality of second discharge electrode plates which are disposed to be spaced apart from each other, and a plurality of second discharge needles which are provided in each of the second discharge electrode plates and generate the plasma discharge. The second ground electrode may include a plurality of second counter electrode plates disposed between the plurality of second discharge electrode plates which are spaced apart from each other.

The first discharge electrode plate and the first counter electrode plate may be disposed to be parallel to the circumferential surface of the first housing, and the second discharge electrode plate and the second counter electrode plate may be disposed to be parallel to the circumferential surface of the second housing.

The plasma sterilization module according to the embodiment of the present disclosure may be provided in the air purifier.

The air purifier may include a main fan which generates an air flow, a discharge guide device which discharges air passing through the main fan and has a discharge grill which is concave downwards, and a flow change device which is movably provided to adjust the flow direction of the air discharged from the discharge grill. The plasma sterilization module may be disposed in the flow change device.

The flow change device may include a flow fan which adjusts the flow direction of the air discharged from the discharge grill, and the plasma sterilization module may be disposed in the flow change device. The first discharge module may be disposed on the upstream of the flow fan, and the second discharge module may be disposed on the downstream of the flow fan.

The plasma sterilization module according to the embodiment of the present disclosure may be provided in the air conditioner.

Specific details of other embodiments are included in the detailed description and drawings.

Advantageous Effects

A plasma sterilization module of the present disclosure has one or more effects as follows.

First, a discharge electrode and a ground electrode are disposed such that air passes through an area where a plasma discharge occurs, so that charges are accumulated in cell walls while airborne microbes pass through the plasma discharge area, and the cell walls of the microbes are broken by the Coulomb force due to the charges, thus improving sterilization performance.

Second, two or more stages of discharge electrodes are provided, or two or more stages of discharge modules each having a discharge electrode and a ground electrode are provided in an air flow direction, a high negative voltage is applied to a first discharge electrode located on an upstream side of an air flow path to generate a glow discharge, a high positive voltage is applied to a second discharge electrode located on a downstream side to generate a streamer discharge, so that airborne microbes are sterilized and charged with negative charges on a first stage, and then are sterilized with a potential difference being maximized on a second stage, thus significantly improving sterilization performance.

Third, as compared with a conventional discharge unit using radical diffusion, bacteria removal performance is improved, so that it is possible to reduce the concentration of ozone generated by a plasma discharge.

Fourth, microbes are sterilized by charges, so that a separate catalytic means is not required, and a housing having a first surface through which air is introduced and a second surface which is opposite to the first surface and through which air is discharged is disposed on a flow path through which air flows, and a discharge electrode and a ground electrode are disposed such that air passes through an area where a plasma discharge occurs, thus reducing a pressure difference between an upstream side and a downstream side of the air flow path and thereby improving sterilization performance and blowing performance.

Fifth, a discharge electrode includes a discharge needle where a plasma discharge occurs, a plurality of discharge electrode plates on which the discharge needle is disposed, and a discharge-electrode support portion connecting the discharge electrode plates, and a ground electrode includes a plurality of counter electrode plates disposed between the discharge electrode plates which are spaced apart from each other and connecting the counter electrode plates, so that it is possible to manufacture a structure in which a shape is repeated, and thereby the degree of freedom in shape is increased, so that the present disclosure may be applied to various shapes of air purifiers and air conditioners, and may apply a plurality of modules to an air purifier and an air conditioner.

Effects of the present disclosure are not limited to the above-mentioned effects, and other effects that are not mentioned will be clearly understood by those skilled in the art from the claims.

BRIEF DESCRIPTION OF THE DRAWINGS

FIGS. 10A and 10B are conceptual views showing the shapes of plasma discharge, in which A shows a case where a positive voltage is applied to the discharge electrode, and B shows a case where a negative voltage is applied to the discharge electrode.

DESCRIPTION OF EXEMPLARY EMBODIMENTS

Figure 1:
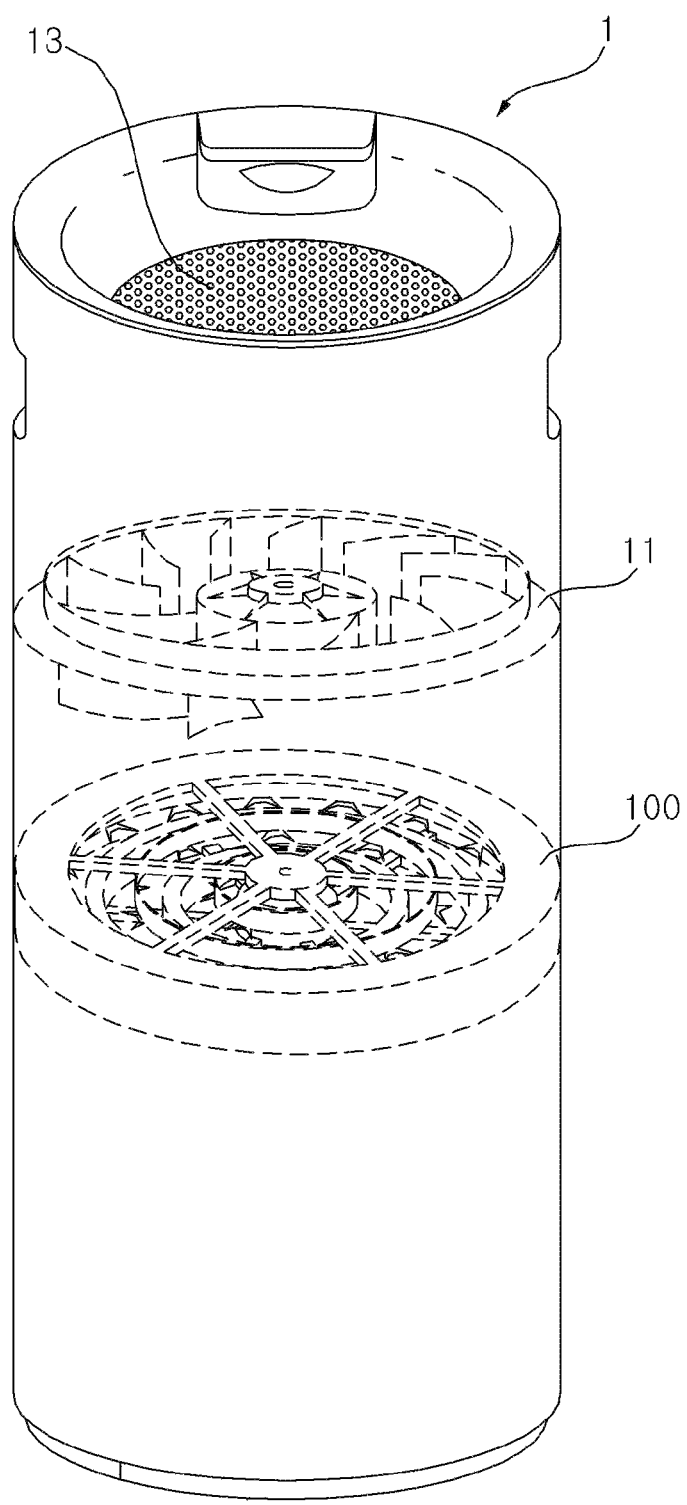
FIG. 1 is a front view of an air purifier having a plasma sterilization module in accordance with a first embodiment of the present disclosure.

Advantages and features of the present disclosure and a method for accomplishing the advantages and features will become apparent with reference to embodiments that will be described below in detail together with the accompanying drawings. However, the present disclosure may be implemented in various forms without being limited to embodiments that will be described below. These embodiments are provided to make the disclosure of the present disclosure complete and to make those skilled in the art completely understand the scope of the present disclosure. The present disclosure is merely defined by the scope of the claims. The same reference numerals are used to designate the same components throughout the specification.

Figure 2:
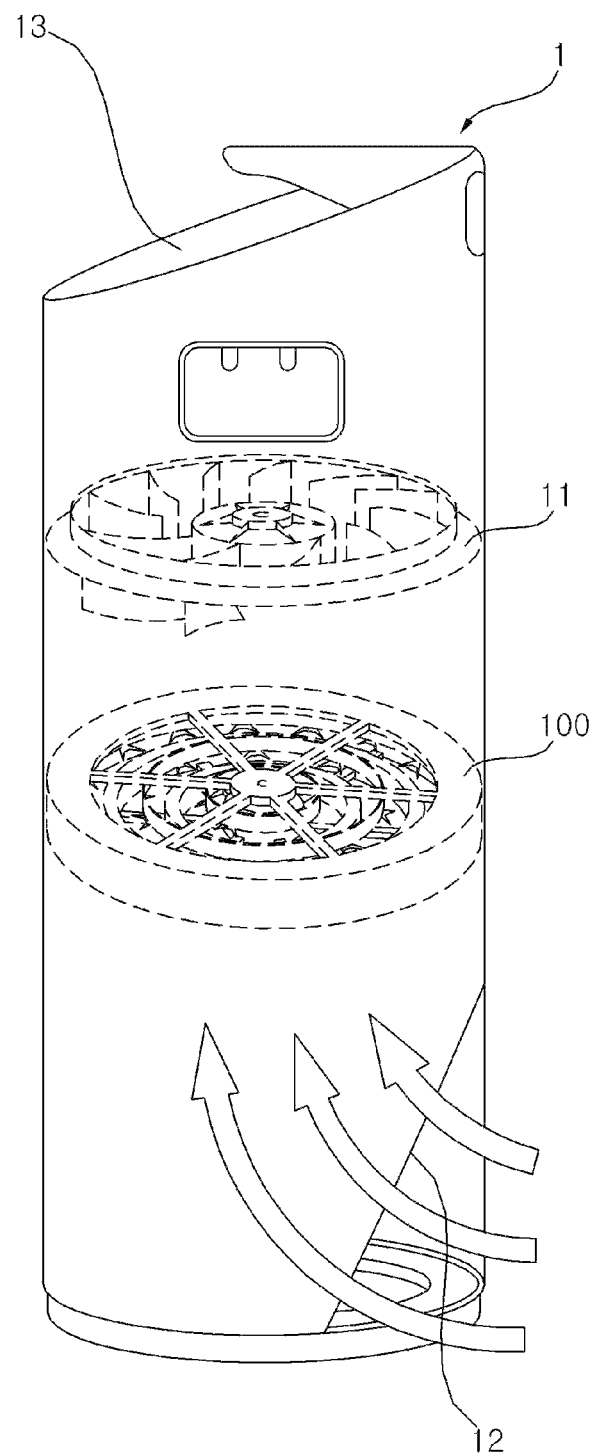
FIG. 2 is a side view of the air purifier illustrated in FIG. 1.
Figure 3:
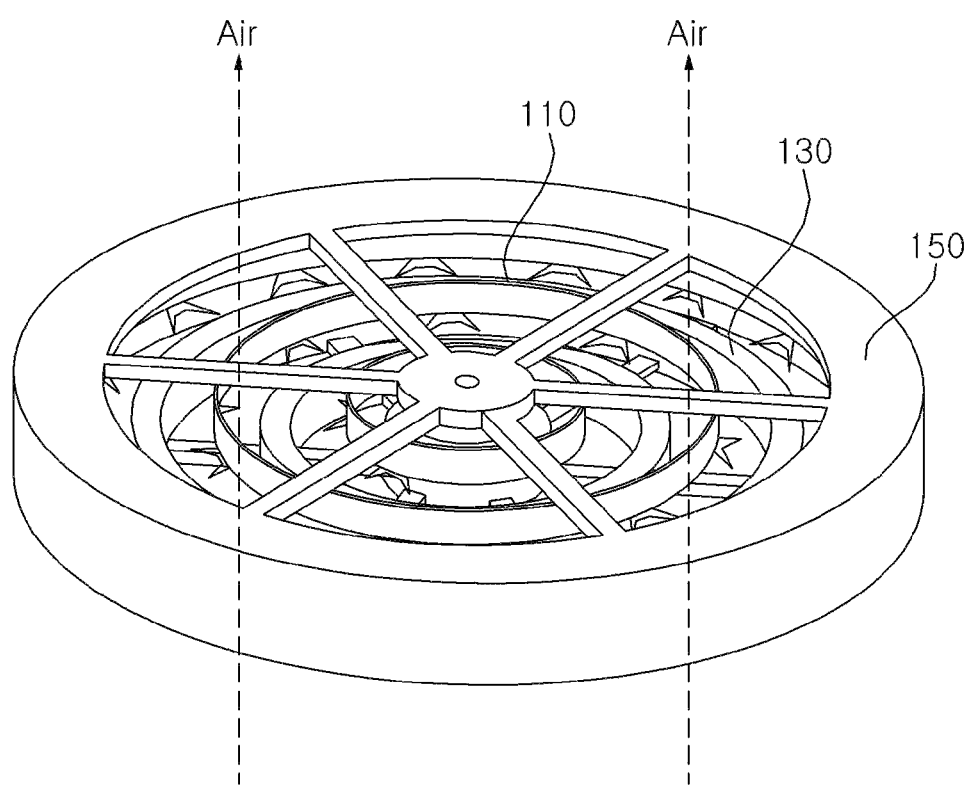
FIGS. 3 and 4 are perspective views of the plasma sterilization module in accordance with the first embodiment of the present disclosure.
Figure 4:
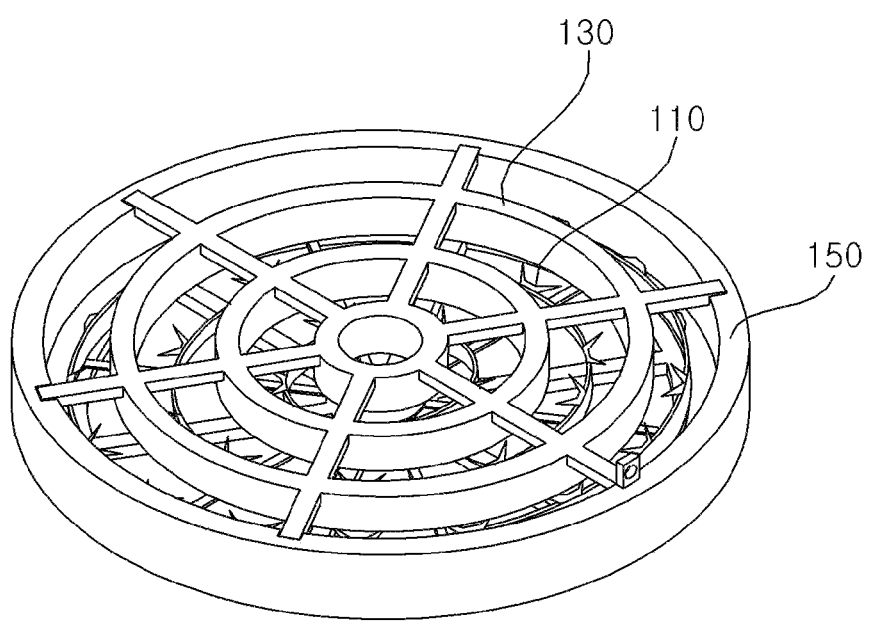
Figure 5:
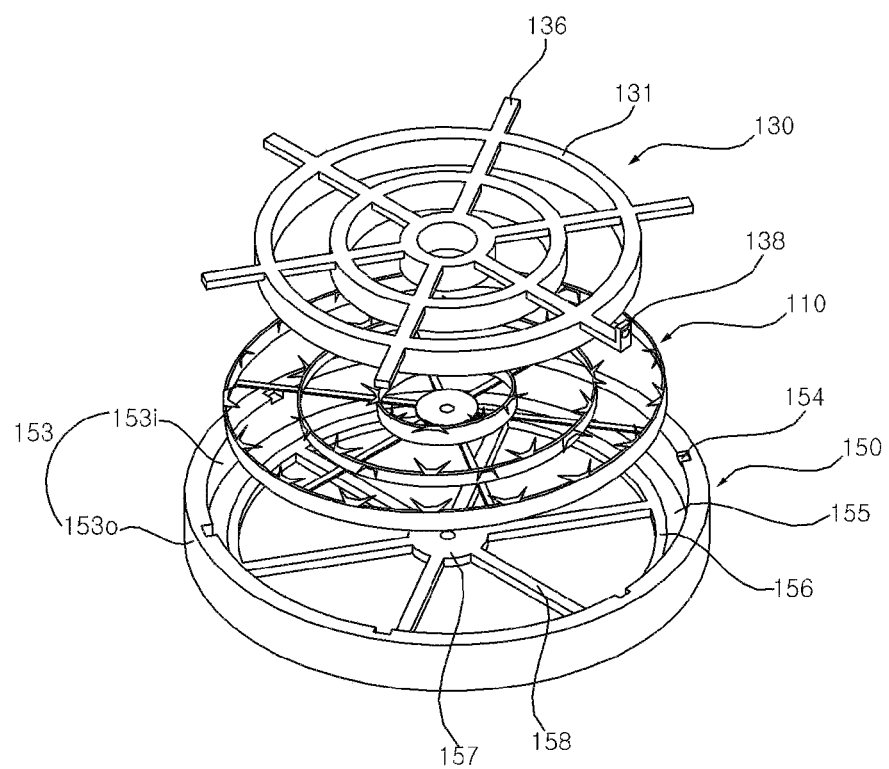
FIG. 5 is an exploded perspective view of the plasma sterilization module illustrated in FIG. 4.
Figure 6:
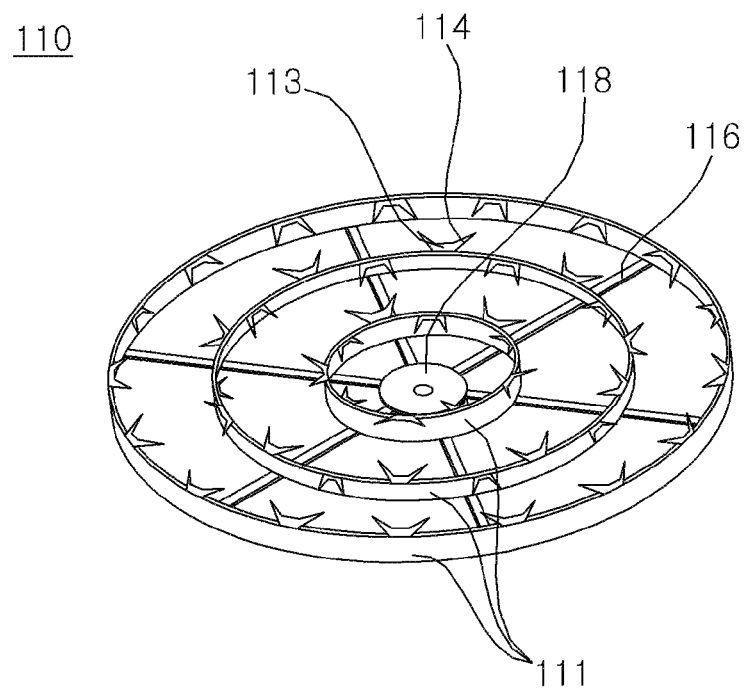
FIG. 6 is a perspective view of a discharge electrode illustrated in FIG. 5.
Figure 7:
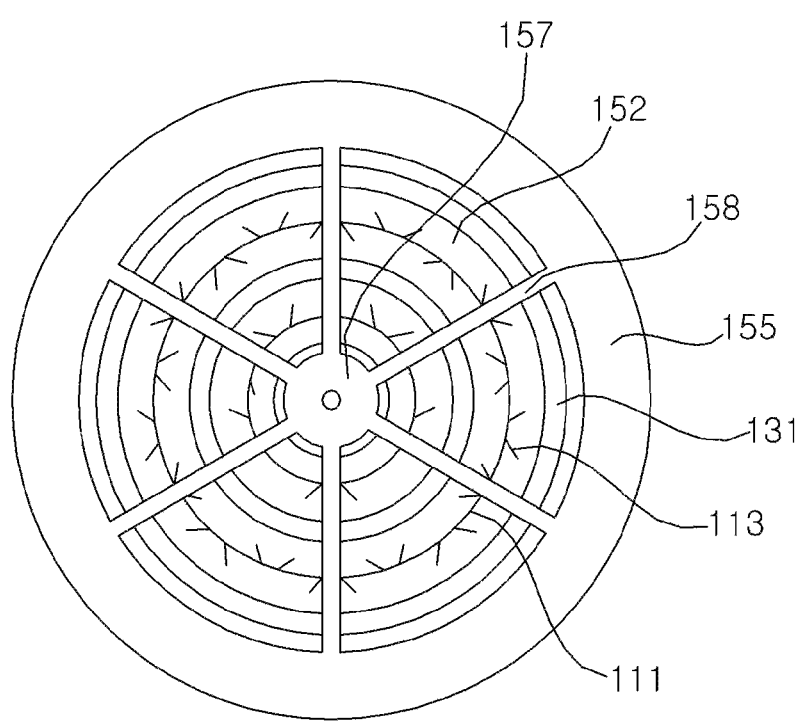
FIG. 7 is a plan view of the plasma sterilization module in accordance with the first embodiment of the present disclosure.
Figure 8:
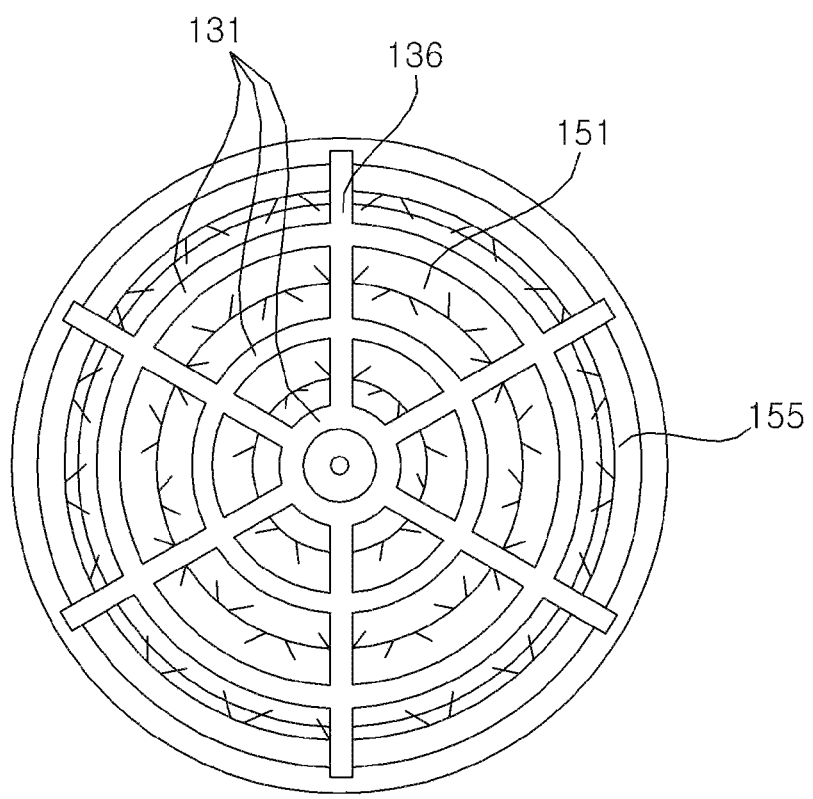
FIG. 8 is a bottom view of the plasma sterilization module in accordance with the first embodiment of the present disclosure.

FIG. 1 is a front view of an air purifier having a plasma sterilization module 100 in accordance with an embodiment of the present disclosure. FIG. 2 is a side view of the air purifier illustrated in FIG. 1.

Referring to FIGS. 1 and 2, the air purifier 1 in accordance with the first embodiment of the present disclosure may include a cylindrical body, an inlet port 12 provided on a lower portion of the body to introduce air, an outlet port 13 provided on an upper portion of the body to discharge the air introduced into the inlet port 12, a blower fan 11 provided in the body to cause the air to flow from the inlet port 12 to the outlet port 13, and a plasma sterilization module 100 sterilizing the introduced air using a plasma discharge.

The air purifier 1 may be configured such that the inlet port 12 into which the air is introduced is provided under the plasma sterilization module 100 and the outlet port 13 from which the air is discharged is provided above the plasma sterilization module 100.

Furthermore, the blower fan 11 may be disposed to cause the air to flow to the upper side of the plasma sterilization module 100. In this case, the outlet port 13 may be formed above the blower fan 11. In other words, the blower fan 11 may be disposed between the plasma sterilization module 100 and the outlet port 13.

The shape of the air purifier 1 shown in FIGS. 1 and 2 is merely illustrative, and the present disclosure is not limited thereto.

Meanwhile, a motor (not shown) for driving the blower fan 11, various circuit components, a filter, etc. may be accommodated in the body of the air purifier 1. The blower fan 11 may function to suck contaminated air from an outside and discharge purified air to the outside again.

The blower fan 11 may be provided above the plasma sterilization module 100 to cause the air to flow from the lower side of the plasma sterilization module 100 to the upper side of the plasma sterilization module 100. Thus, the air may flow sequentially through the inlet port 12, the plasma sterilization module 100, and the outlet port 13. Furthermore, various filters may be disposed between the inlet port 12 and the blower fan 11.

The plasma sterilization module 100 may be disposed in the body to sterilize and purify the air introduced into the inlet port 12. A circumference of the plasma sterilization module 100 may be formed to have the same shape as an inner circumference of the body.

Hereinafter, the plasma sterilization module 100 in accordance with the first embodiment of the present disclosure will be described in detail with reference to the accompanying drawings.

The plasma sterilization module 100 in accordance with the first embodiment of the present disclosure includes a housing 150 which is disposed on a flow path through which air flows, and has a first surface 151 into which the air is introduced and a second surface 152 which is opposite to the first surface 151 and through which the introduced air is discharged, a discharge electrode 110 which is disposed in the housing 150, and a ground electrode 130 which is disposed in the housing 150 and is spaced apart from the discharge electrode 110.

A circumferential surface 153 of the housing 150 which forms the opened first surface 151 and second surface may be formed parallel to the flow path through which the air flows. The housing 150 may be disposed in the air purifier 1, an air conditioner, etc. to which the plasma sterilization module 100 is applied, and may be disposed to come into contact with a surface forming the air flow path in the body of the air purifier 1 or the air conditioner. Therefore, the air introduced into the inlet port 12 may completely pass through the plasma sterilization module 100 and then flow to the outlet port 13.

A high voltage is applied to the discharge electrode 110 to generate a plasma discharge towards the ground electrode 130 between the first surface 151 and the second surface 152. The discharge electrode 110 is supplied with the high voltage to generate the plasma discharge, and the ground electrode 130 provides a ground to the plasma sterilization module 100 to cause the plasma discharge generated by the discharge electrode 110 to be generated towards the ground electrode 130.

The discharge electrode 110 may include a plurality of discharge electrode plates 111, a plurality of discharge needles 113 provided in each of the discharge electrode plates 111 and generating a plasma discharge, and a discharge-electrode support portion 116 connecting the plurality of discharge electrode plates 111. The discharge electrode plates 111 and the discharge needles 113 may be integrally formed.

The plurality of discharge electrode plates 111, the plurality of discharge needles 113, and the discharge-electrode support portion 116 may be made of conductive material. The discharge needles 113 may be provided on the discharge electrode plates 111, and the plurality of discharge electrode plates 111 may be connected via the discharge-electrode support portion 116, so that the same voltage may be applied to the plurality of discharge needles 113 even if a voltage is applied to any portion of the discharge electrode 110.

The discharge electrode 110 may include a voltage application portion 118 supplied with a high voltage and connected to the plurality of discharge electrode plates 111. The voltage application portion 118 and the plurality of discharge electrode plates 111 may be connected by the discharge-electrode support portion 116.

The plurality of discharge electrode plates 111 may be spaced apart from each other, and may be disposed to have a constant distance between neighboring discharge electrode plates 111. The ground electrode 130 may be disposed between the plurality of discharge electrode plates 111 which are spaced apart from each other.

The ground electrode 130 may include a counter electrode plate 131 disposed between the plurality of discharge electrode plates 111 which are spaced apart from each other, and a ground-electrode support portion 136 which is connected to the counter electrode plate 131 and is disposed to be supported by the housing 150. The ground electrode 130 may include a plurality of counter electrode plates 131.

The counter electrode plate 131 may be disposed to be opposite to the discharge electrode plate 111. The counter electrode plate 131 may be disposed in a center between the plurality of discharge electrode plates 111 which are spaced apart from each other. The plurality of discharge electrode plates 111 and the plurality of counter electrode plates 131 may be arranged to maintain the same distance between the discharge electrode plate 111 and the counter electrode plate 131 which are adjacent to each other.

The plurality of counter electrode plates 131 may be connected to each other by the ground-electrode support portion 136. The plurality of counter electrode plates 131 and the ground-electrode support portion 136 may be formed of conductive material, and may be connected to each other to have the same potential. Therefore, even if a voltage is applied to any portion of the ground electrode 130, it may have the same potential. Further, even if a ground is provided to any portion of the ground electrode 130, the entire ground electrode 130 may provide a ground to the plasma sterilization module 100.

Meanwhile, the discharge electrode 110 and the ground electrode 130 are disposed such that air introduced into the first surface 151 passes through the area where the plasma discharge occurs, and then is discharged to the second surface 152. The plasma discharge may occur across air introduced into the first surface 151 and discharged to the second surface 152.

The discharge electrode 110 and the ground electrode 130 may be disposed to be parallel to the circumferential surface 153 of the housing 150. The plurality of discharge electrode plates 111 and the plurality of counter electrode plates 131 may be disposed to be parallel to the circumferential surface 153 of the housing 150.

The discharge electrode 110 and the ground electrode 130 may be disposed such that the area where the plasma discharge occurs intersects with a direction in which the air flows. The discharge electrode 110 and the ground electrode 130 may be disposed such that the area where the plasma discharge occurs is perpendicular to the direction in which the air flows. The area where the plasma discharge occurs may be perpendicular to the direction in which the air flows.

A width of each of the discharge electrode plate 111 and the counter electrode plate 131 may be defined as a direction perpendicular to the air flow direction, and a height thereof may be defined as a direction parallel to the air flow direction. In this case, the discharge electrode plate 111 and the counter electrode plate 131 may be formed such that the width thereof is smaller than the height thereof. Therefore, the discharge electrode 110 and the ground electrode 130 do not obstruct the flow of the air which is introduced into the first surface 151 of the housing 150 and then is discharged to the second surface 152, thus reducing a pressure difference between the upstream and the downstream of the air flow path compared to the related art.

Meanwhile, the discharge needle 113 may protrude towards the counter electrode plate 131, and the plurality of discharge needles 113 may have the same protruding distance from the discharge electrode plate 111. The plurality of discharge needles 113 may have the same size and shape.

Among the plurality of discharge needles 113, the plurality of discharge needles 113 provided on the discharge electrode plate 111 disposed between the plurality of counter electrode plates 131 protrude towards the counter electrode plate 131. Alternately, the discharge needles may protrude towards the counter electrode plate 131 disposed inside the discharge electrode plate 111 and the counter electrode plate 131 disposed outside the discharge electrode plate 111.

That is, any one discharge needle 113 may protrude towards an inner counter electrode plate 131, two discharge needles 113 adjacent thereto may protrude towards an outer counter electrode plate 131, and a discharge needle 113 adjacent to the outwardly protruding discharge needle 113 may protrude inwards. In other words, the plurality of discharge needles 113 protruding outwards may be disposed between the plurality of discharge needles 113 protruding inwards, and the plurality of discharge needles 113 protruding inwards may be disposed between the plurality of discharge needles 113 protruding outwards.

Since the discharge electrode plates 111 and the counter electrode plates 131 are alternately disposed, the discharge electrode plate 111 or the counter electrode plate 131 may be disposed at an outermost portion inside the housing 150, i.e. at a position closest to the circumferential surface 153 of the housing 150. When the discharge electrode plate 111 is disposed at the outermost portion inside the housing 150, the discharge needle 113 provided on the discharge electrode plate 111 disposed at the outermost portion may protrude towards the inner counter electrode plate 131.

Depending on the shape of the discharge electrode plate 111 and the counter electrode plate 131, the discharge electrode plate 111 or the counter electrode plate 131 may be present at an inner portion. For example, the plasma sterilization module 100 has the discharge electrode plate 111 and the counter electrode plate 131 forming concentric circles, the discharge electrode plate 111 or the counter electrode plate 131 may be disposed at the innermost portion. The same applies to a polygonal shape as well as a circular shape. In FIGS. 3 to 8, the counter electrode plate 131 is disposed at the innermost portion. However, unlike this, the discharge electrode plate 111 may be disposed at the innermost portion.

When the discharge electrode plate 111 is disposed at the innermost portion, i.e., a position closest to the center of the housing 150, the discharge needles 113 provided on the discharge electrode plate 111 may protrude towards the outer ground electrode 130.

The discharge needle 113 may have a tip 114 whose end facing the counter electrode plate 131 is pointed. If a high voltage is applied to the discharge electrode 110, a plasma discharge is generated from the tip 114 towards the counter electrode plate 131.

The discharge needle 113 may have two tips 114 which are symmetrical to each other. When the discharge needle 113 has two tips 114, it is easy to manufacture the discharge electrode 110 having the plurality of discharge needles 113, and it is possible to reduce the unnecessary waste of material.

The discharge electrode plate 111 and the discharge needle 113 may be made from a single flat plate. When a central portion of the flat plate having a width which is larger than a sum of a height twice the height of the discharge electrode plate 111 and the height of the discharge needle 113 is cut such that inverted trapezoidal portions engage with each other, it is possible to manufacture a pair of discharge electrode plates 111 having the plurality of discharge needles 113, and the discharge needle 113 may be made by bending the inverted trapezoidal portion towards the ground electrode 130. In this case, a manufacturing process is simplified and the waste of material is reduced, so that it can be economical.

The discharge needle 113 may have two tips 114, and the two tips 114 may protrude towards the ground electrode 130 in the same direction. In this case, two tips 114 provided on any one discharge needle 113 may protrude towards the inner ground electrode 130, and two tips 114 provided on a discharge needle 113 adjacent to the discharge needle 113 may protrude towards the outer ground electrode 130.

Alternatively, any one of the two tips 114 provided on any one discharge needle 113 may protrude towards the inner ground electrode 130, and the other may protrude towards the outer ground electrode 130. In this case, a plurality of tips 114 may alternately protrude towards the inner ground electrode 130 and the outer ground electrode 130.

The plurality of discharge needles 113 may be formed to have the same size and shape. Since a distance between the discharge electrode plate 111 and the counter electrode plate 131 is constant and the discharge needles 113 have the same size and shape, the discharge electrode 110 and the ground electrode 130 may be disposed to have a constant distance therebetween. In other words, distances between the tips 114 of the plurality of discharge needles 113 and the facing counter electrode plate 131 may be constant. The plasma discharge may occur between the tip 114 of the discharge needle 113 and the facing counter electrode plate 131.

Meanwhile, the intensity of the plasma discharge is determined depending on a distance between the discharge electrode 110 and the ground electrode 130, the diameter of the tip 114, and the level of applied voltage. The plasma sterilization module 100 in accordance with the embodiment of the present disclosure may generate the plasma discharge of uniform intensity, because the distance between the discharge electrode 110 and the ground electrode 130, the diameter of the tip 114, and the level of applied voltage remain the same in all areas where the plasma discharge occurs.

The discharge electrode 110 and the ground electrode 130 may be formed of material having excellent conductivity. The discharge electrode 110 may be formed of stainless steel.

As the plasma sterilization module 100 is used, the electrode may be worn. In particular, the tip 114 of the discharge needle 113 may be worn. The abrasion of the tip 114 causes the diameter of an end portion to become thick, and causes a change in distance between the discharge electrode and the ground electrode, thus negatively affecting the intensity of the plasma discharge. Therefore, as the plasma sterilization module 100 is used, the intensity of the plasma discharge may become non-uniform.

When the electrode is plated with nickel-cobalt alloy, it is known that this plating can prevent the electrode from being worn. In order to prevent the electrode from being worn out, outer surfaces of the discharge electrode 110 and the ground electrode 130 may be plated with the nickel-cobalt alloy. Particularly, the discharge electrode 110 having the tip 114 may be plated with the nickel-cobalt alloy. An outer surface of at least a portion of the discharge electrode 110 where the plasma discharge occurs may be plated with nickel-cobalt alloy. In other words, the discharge needle 113 may be plated with nickel-cobalt alloy. The tip 114 of the discharge needle 113 may be plated with nickel-cobalt alloy.

Referring to FIGS. 3 to 9, the plasma sterilization module 100 in accordance with the first embodiment of the present disclosure includes a housing 150 disposed on a flow path through which air flows, and having a first surface 151 into which the air is introduced and a second surface 152 which is opposite to the first surface 151 and through which the introduced air is discharged, a discharge electrode 110 disposed in the housing 150, and a ground electrode 130 disposed in the housing 150 and spaced apart from the discharge electrode 110.

The housing 150 of the plasma sterilization module 100 in accordance with the first embodiment of the present disclosure may be formed in the shape of a cylinder in which the first surface 151 and the second surface 152 are opened. The housing 150 may include a rim surface 155 which protrudes inwards from an inner circumferential surface 153i (hereinafter, referred to as an inner circumference) and is located in either of the first surface 151 or the second surface 152, a hub ring 157 located in the center of either of the first surface 151 or the second surface 152, and radial spokes 158 connecting the rim surface 155 and the hub ring 157. Hereinafter, a case where the rim surface 155 and the hub ring 157 are located in the second surface 152 will be described as an example.

The housing 150 may have a guide groove 154 formed in the first surface 151 or the second surface 152 where the rim surface 155 is not located, the guide groove being recessed outwards from the inner circumference 153i. When the rim surface 155 is located in the second surface 152, the guide groove 154 may be formed to be recessed outwards from an end of the inner circumference 153i of the housing 150 in the proximity of the first surface 151.

The housing 150 may be formed such that the circumferential surface 153 forming the opened first and second surfaces 151 and 152 is parallel to the flow path through which air flows. An outer circumferential surface 153o (hereinafter, referred to as an outer circumference) of the housing 150 may be disposed to be in contact with a surface forming the air flow path in a body of an air purifier 1 or an air conditioner to which the plasma sterilization module 100 is applied.

When the inlet port 12 is disposed on the lower portion of the body of the air purifier 1 or the air conditioner to which the plasma sterilization module 100 in accordance with the first embodiment of the present disclosure is applied, and the outlet port 13 is disposed on the upper portion of the body, the housing 150 may be disposed such that the first surface 151 faces downwards and the second surface 152 faces upwards.

The discharge electrode 110 of the plasma sterilization module 100 in accordance with the first embodiment of the present disclosure may include a plurality of ring-shaped discharge electrode plates 111 which form concentric circles around the central axis of the housing 150. The number of the discharge electrode plates 111 may vary depending on the size of the housing 150.

The discharge electrode 110 may include a voltage application portion 118 to which a high voltage is applied, and the voltage application portion 118 may be seated on the hub ring 157 of the housing 150. A high voltage may be applied to the voltage application portion 118 through a hole formed in the center of the hub ring 157. Furthermore, the voltage application portion 118 may have a hole which communicates with the hole formed in the center of the hub ring 157.

A bolt may be inserted into both the hole formed in the center of the hub ring 157 and the hole formed in the center of the voltage application portion 118 to fasten the discharge electrode 110 to the housing 150. An electric wire connected to a power supply for applying a high voltage may be connected to the bolt to apply the high voltage to the discharge electrode 110. Means for applying the high voltage to the discharge electrode 110 are not limited thereto, and various known means may be used.

The discharge electrode 110 or the ground electrode 130 may be located at a position closest to the circumferential surface 153 of the housing 150. As shown in FIGS. 3 to 9, when the discharge electrode 110 is disposed at the position closest to the circumferential surface 153 of the housing 150, the discharge electrode plate 111 located on the outermost side among the discharge electrode plates 111 may be disposed to be seated on the rim surface 155 of the housing 150. An inner end of the rim surface 155 is formed to be stepped and has a seating groove 156 which guides the position of the discharge electrode plate, and the discharge electrode plate 111 located on the outermost side may be supported to be in contact with the seating groove 156. The discharge needles 113 protruding from the discharge electrode plate 111 located on the outermost side may protrude towards the inner ground electrode 130.

The discharge electrode 110 may include the discharge-electrode support portion 116 which connects the plurality of discharge electrode plates 111 to each other. The discharge-electrode support portion 116 may be seated on the spoke 158. The discharge-electrode support portion 116 is disposed to come into contact with the voltage application portion 118 and the plurality of discharge electrode plate 111, and connects the voltage application portion to the discharge electrode plate to apply a high voltage applied to the voltage application portion 118 to the discharge electrode plate 111. The voltage application portion 118 and the discharge-electrode support portion 116 may be formed to have shapes corresponding to those of the hub ring 157 and the spoke 158, respectively.

As shown in FIGS. 3 to 8, the discharge needle 113 may have two tips 114 which are symmetrical to each other, and two tips 14 provided on one discharge needle 113 may protrude towards the ground electrode 130 in the same direction. Two tips 114 of any one discharge needle 113 among the discharge needles 113 formed on the discharge electrode plate 111 disposed between the plurality of counter electrode plates 131 may protrude towards the inner ground electrode 130, while two tips 114 provided on the discharge needle 113 adjacent to the above-described discharge needle 113 may protrude towards the outer ground electrode 130.

The ground electrode 130 of the plasma sterilization module 100 in accordance with the first embodiment of the present disclosure may include counter electrode plates 131 disposed between the plurality of discharge electrode plates 111 which are spaced apart from each other, and ground-electrode support portions 136 which connect the plurality of counter electrode plates 131 to each other. The counter electrode plates 131 may form concentric circles around the central axis of the housing 150 together with the discharge electrode plates 111. The number of the counter electrode plates 131 may vary depending on the number of the discharge electrode plates 111. Although three discharge electrode plates 111 and three counter electrode plates 131 are provided in the drawing showing the first embodiment of the present disclosure, the present disclosure is not limited thereto.

The counter electrode plates 131 may be disposed in centers between the plurality of discharge electrode plates 111 which are spaced apart from each other. The distances between the plurality of discharge needles 113 and the counter electrode plates 131 may be uniform.

The ground-electrode support portions 136 are radially formed to extend outwards from the innermost counter electrode plate 131, connect the plurality of counter electrode plates 131 to each other, and protrude outwards from the outermost counter electrode plate 131 such that the ground electrode 130 is supported by the housing 150. The ground electrode 130 may include the plurality of ground-electrode support portions 136. Outer ends of the ground-electrode support portions 136 may be seated in the guide grooves 154. Each ground-electrode support portion 136 may be formed to have a shape corresponding to those of the spoke 158 and the discharge-electrode support portion 116.

Three or more spokes 158, discharge-electrode support portions 116, and ground-electrode support portions 136 may be provided to allow the discharge electrode 110 and the ground electrode 130 to be stably seated in the housing 150. Although six spokes 158, six discharge-electrode support portions 116, and six ground-electrode support portions 136 are illustrated in the drawing showing the first embodiment of the present disclosure, the present disclosure is not limited thereto.

A ground connector 138 may be formed on an outer end of at least any one of the plurality of ground-electrode support portions 136. The ground connector 138 may protrude to be perpendicular to the outer end of the ground-electrode support portion 136, and a hole may be formed in a center of the ground connector. The ground connector 138 may be connected to a ground electrode of a commercial power supply or may be connected to a control circuit board of the air purifier 1 or the air conditioner to which the plasma sterilization module 100 is applied, thus providing a ground to the ground electrode 130.

The discharge electrode 110 may be supported by the rim surface 155 inside the housing 150 to be disposed on the second surface 152, the ground electrode 130 may be supported by the guide groove 154 to be disposed on the first surface 151, and the discharge electrode 110 and the ground electrode 130 may be lower in height than the housing 150 to be accommodated in the housing 150. The discharge electrode 110 and the ground electrode 130 are disposed on opposite sides of the housing 150, are lower in height than the housing 150, and are disposed such that at least portions thereof face each other.

Figure 9:
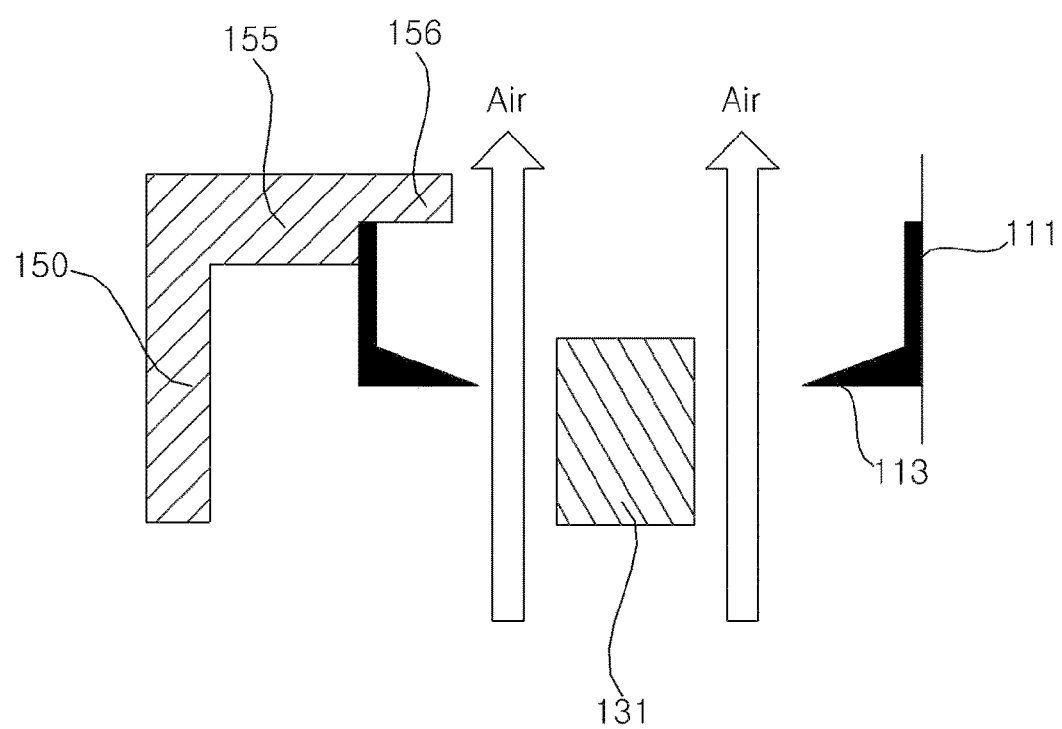
FIG. 9 is a conceptual view showing air which passes through a plasma discharge area occurring in a portion of the plasma sterilization module in accordance with the embodiment of the present disclosure.

As shown in FIG. 9, the discharge electrode 110 and the ground electrode 130 may be disposed such that the discharge needle 113 and the counter electrode plate 131 face each other. The lower surface of the counter electrode plate 131 may be disposed at a position lower than the discharge needle 113, and the upper surface of the counter electrode plate 131 may be disposed at a position higher than the discharge needle 113.

The plasma sterilization module 100 in accordance with the embodiment of the present disclosure may be disposed such that the first surface 151 and the second surface 152 are perpendicular to the air flow direction. The discharge electrode 110 and the ground electrode 130 may be disposed such that the area where the plasma discharge occurs is perpendicular to the air flow direction.

Therefore, a pressure difference between the upstream and the downstream of the air flow path is small, and air passing through the plasma sterilization module 100 can be effectively sterilized.

The sterilizing operation using the plasma discharge of the plasma sterilization module 100 according to the present disclosure configured as described above will be described as follows.

Figure 11:
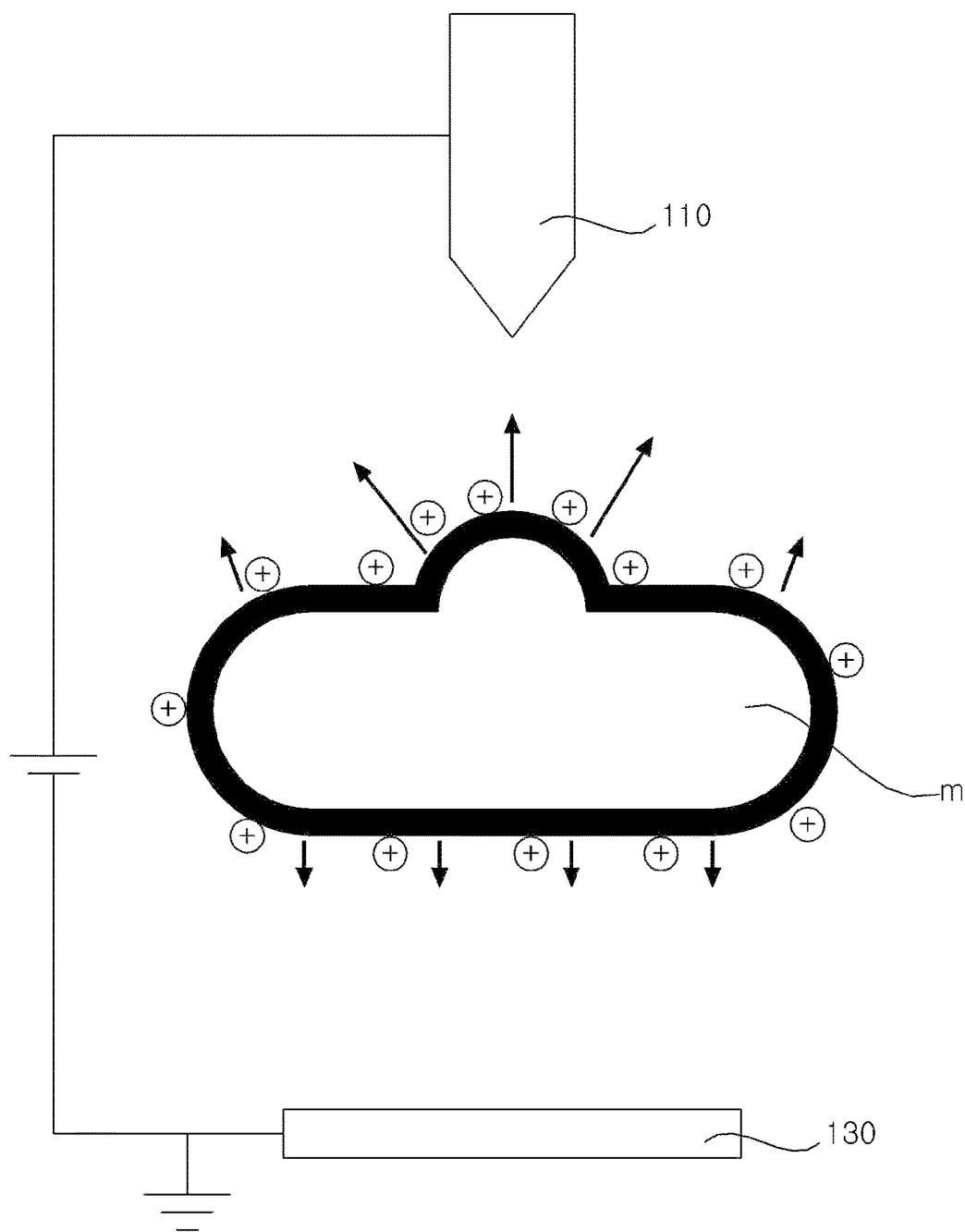
FIG. 11 is a conceptual view showing the sterilization principle of air which passes through the plasma discharge area of the plasma sterilization module in accordance with the embodiment of the present disclosure.

FIG. 10(*a*) is a conceptual view showing the shape of the plasma discharge when a positive voltage is applied to the discharge electrode, FIG. 10(*b*) is a conceptual view showing the shape of the plasma discharge when a negative voltage is applied to the discharge electrode, and FIG. 11 is a conceptual view showing the sterilization principle of air which passes through the plasma discharge area of the plasma sterilization module in accordance with the embodiment of the present disclosure.

The shape of the plasma discharge (or, corona discharge) is changed by a potential difference between the discharge electrode 110 and the counter electrode (or, ground electrode). If a positive electrode of the power supply is connected to the discharge electrode 110 and the level of applied voltage is increased, the discharge shape is gradually changed to the shape of a2, a3, a4, and a5 of FIG. 10(*a*). In FIG. 10(*a*), a2 shows a glow discharge, a3 shows a brush discharge, a4 shows a streamer discharge, and a5 shows an arc discharge.

If a negative electrode of the power supply is connected to the discharge electrode 110 and the level of the applied voltage is increased, the discharge shape is gradually changed to the shape of b2 and b3 of FIG. 10(*b*). Here, b2 shows a glow discharge, and b3 shows an arc discharge. When the negative electrode of the power supply is connected to the discharge electrode, the streamer discharge does not occur unlike the case where the positive electrode of the power supply is connected to the discharge electrode.

The positive voltage may be applied by connecting the positive electrode of the power supply to the discharge electrode 110 of the plasma sterilization module 100 according to the embodiment of the present disclosure. A high positive voltage may be applied to the discharge electrode 110 to generate the streamer discharge towards the ground electrode 130. The streamer discharge causes an electron avalanche when more electric energy is applied in the glow discharge, forms a discharge area wider than that of the glow discharge, and is advantageous for sterilization treatment.

While airborne microbes m passing through the plasma sterilization module 100 pass through the discharge area between the discharge electrode 110 and the ground electrode 130, charges are accumulated in cell walls. The metabolism of the microbes m becomes impossible because the tension of the cell walls is broken by the Coulomb force of the charges and the cell walls are torn. Thus, the air is sterilized.

In order to measure the sterilization performance of the plasma sterilization module 100 according to an embodiment of the present disclosure, air flows through the plasma sterilization module 100 at a flow rate of 1 m/s, and the concentration of microbes m present in an upstream area before the air passing through the plasma sterilization module 100 is compared with the concentration of microbes m present in a downstream area after the air passing through the plasma sterilization module 100. One-pass sterilization performance measured as such is experimentally observed to be 60% or more. This is similar to the one-pass sterilization performance of UVC LED which is commonly used for the sterilization treatment. Ultraviolet rays are divided into UVA (315 to 400 nm), UVB (280 to 315 nm), and UVC (100 to 280 nm) depending on a wavelength, and the UVC LED refers to an organic light emitting diode using the UVC.

The sterilization performance is also related to time required for air to pass through the plasma discharge area. When the width of the flow path in the area where the plasma discharge occurs is narrower than those of other flow paths, the flow of the air is accelerated, and it is difficult to accumulate sufficient charges in the microbes.

The discharge electrode 110 and the ground electrode 130 of the plasma sterilization module 100 according to the embodiment of the present disclosure are disposed to be parallel to the circumferential surface 153 of the housing, so that a change in width of the air flow path is minimized, charges are sufficiently accumulated in the airborne microbes, and thereby sterilization performance can be improved.

Furthermore, in the case of the conventional sterilization module, the structure of the discharge area interferes with the flow of air, so that a large proportion of air passing through the sterilization module does not pass through the plasma discharge area and only a small proportion of the air passes through the discharge area, and consequently, the sterilization effect realized by the accumulation of the charges is insignificant. Therefore, the related art is problematic in that the sterilization treatment is performed by the diffusion of radicals, so that it is difficult to improve the sterilization performance.

The plasma sterilization module 100 according to the embodiment of the present disclosure is configured such that the first and second surfaces 151 and 152 of the housing 150 are opened, and the discharge electrode 110 and the ground electrode 130 are disposed to be parallel to the circumferential surface 153 of the housing, and thereby the area where the plasma discharge occurs is intersected with the air flow path. Since the air directly passes through the plasma discharge area to perform the sterilization treatment, the sterilization treatment may be performed by applying a voltage lower than that of the related art, and the concentration of generated ozone may be lowered while maintaining the above-described performance.

Generally, the standard of the air purifier for ozone requires the concentration of 30 ppb or less. When the conventional air purifier is used, ozone exceeding the standard concentration may be generated. If the plasma sterilization module 100 according to the embodiment of the present disclosure is applied, ozone may be generated at the level of ⅙ or less of the standard concentration.

Furthermore, unlike the related art, the plasma sterilization module 100 according to the embodiment of the present disclosure is configured such that air to be treated directly passes through the plasma discharge area to sterilize the airborne microbes by the Coulomb force of charges. Thus, a separate catalytic means or dust collecting filter is not required. The catalytic means or the dust collecting filter becomes a factor which increases a pressure difference between the upstream and downstream of the air flow path, and reduces blowing performance. Therefore, as compared with the related art, the plasma sterilization module 100 according to the embodiment of the present disclosure reduces the pressure difference, thus improving the blowing performance. This has effect of increasing the amount of air for the sterilization treatment as compared with the related art.

The plasma sterilization module 100 according to the embodiment of the present disclosure may be applied to the air purifier 1 or the air conditioner 30 having a heat exchanger. When the plasma sterilization module is applied to the air purifier 1, the blower fan 11 causes the air to be introduced through the inlet port 12 into the body of the air purifier 1, and the introduced air passes through the plasma sterilization module 100 to be sterilized, and then is discharged through the outlet port 13 to an outside. When the plasma sterilization module is applied to the air conditioner 30 having the heat exchanger, as in the air purifier 1, the air which is sterilized while passing through the plasma sterilization module 100 performs a heat exchange process with the heat exchanger, and then is discharged to the outside.

Hereinafter, an example where the plasma sterilization module is applied to the air purifier 1 will be described.

The plasma sterilization module 100 is disposed on the flow path through which air flows, in the body of the air purifier 1, and the discharge electrode 110 is connected to the positive electrode of the power supply to generate the plasma discharge towards the ground electrode 130. By applying a high voltage of about 3.5 kV to the discharge electrode 110, the plasma discharge may be generated. The plasma sterilization module 100 is configured such that the first surface 151 which is the upstream side of the flow path through which the air flows, and the second surface 152 which is the downstream side are opened, so that the air directly passes through the plasma discharge area to be sterilized.

The first surface 151 and the second surface 152 of the housing 150 are opened, the discharge electrode plate 111 and the counter electrode plate 131 are disposed to be parallel to the circumferential surface 153 of the housing, and each of the discharge electrode plate 111 and the counter electrode plate 131 is formed such that a width thereof is smaller than a height thereof, so that it does not obstruct the air flow and thereby a reduction in differential pressure may be minimized. In the case of applying the plasma sterilization module 100 of the present disclosure, a reduction in differential pressure which is about ⅙ of a HEPA filter generally applied to the air purifier 1 is realized.

FIG. 12 is a front view of an air purifier 1 having a plasma sterilization module 10 in accordance with a second embodiment of the present disclosure. FIG. 13 is a side view of the air purifier 1 illustrated in FIG. 12.

Referring to FIGS. 12 and 13, the air purifier 1 in accordance with the second embodiment of the present disclosure may include a cylindrical body, an inlet port 12 provided on a lower portion of the body to introduce air, an outlet port 13 provided on an upper portion of the body to discharge the air introduced into the inlet port 12, a blower fan 11 provided in the body to cause the air to flow from the inlet port 12 to the outlet port 13, and plasma sterilization modules 100 and 200 sterilizing the introduced air using a plasma discharge.

The plasma sterilization modules 100 and 200 according to the second embodiment of the present disclosure include a housing 150 which is disposed on a flow path through which air flows, and has a first surface 151 into which the air is introduced and a second surface 152 which is opposite to the first surface 151 and through which the introduced air is discharged, discharge electrodes 110 and 210 which are disposed in the housing 150, and a ground electrode 130 which is disposed in the housing 150 and is spaced apart from the discharge electrodes 110 and 210.

The discharge electrodes 110 and 210 include a first discharge electrode 110 which is supplied with a high voltage to generate a plasma discharge towards the ground electrode 130, and a second discharge electrode 210 which is disposed downstream of the air flow path compared to the first discharge electrode 110 and is supplied with a high voltage to generate a plasma discharge towards the ground electrode 130.

The first discharge electrode 110 may include a plurality of first discharge electrode plates 111, a plurality of first discharge needles 113 provided in each of the first discharge electrode plates 111 and generating the plasma discharge, and a first discharge-electrode support portion 116 connecting the plurality of first discharge electrode plates 111. The first discharge electrode plates 111 and the first discharge needles 113 may be integrally formed.

The second discharge electrode 210 may include a plurality of second discharge electrode plates 211, a plurality of second discharge needles 213 provided in each of the second discharge electrode plates 211 and generating the plasma discharge, and a second discharge-electrode support portion 216 connecting the plurality of second discharge electrode plates 211. The second discharge electrode plates 211 and the second discharge needles 213 may be integrally formed. The second discharge electrode 210 may be formed to have the same shape as the first discharge electrode 110.

The above description of the discharge electrode 110 of the first embodiment may be applied to the first and second discharge electrodes 110 and 210 of this embodiment.

Since each component of the second discharge electrode is the same as each component of the first discharge electrode, a duplicated description of the same components will be omitted below.

The second discharge electrode 210 may be spaced apart from the first discharge electrode 110, and the second discharge electrode may be electrically separated from the first discharge electrode, so that different voltages may be applied to the first and second discharge electrodes.

The first discharge electrode 110 may include a first voltage application portion 118 supplied with a high voltage and connected to the plurality of first discharge electrode plates 111. The first voltage application portion 118 and the plurality of first discharge electrode plates 111 may be connected by the first discharge-electrode support portion 116. The second discharge electrode 210 may include the second voltage application portion 218.

The first discharge needle 113 may have two tips 114, and the two tips 114 may protrude towards the ground electrode 130 in the same direction. In this case, two tips 114 provided on any one first discharge needle 113 may protrude towards an inner ground electrode 130, and two tips 114 provided on a first discharge needle 113 adjacent to the above-described first discharge needle 113 may protrude towards an outer ground electrode 130. The above description of the tip 114 provided on the first discharge needle 113 is also applied to the tip 214 provided on the second discharge needle 213.

The ground electrodes 130 may be configured as follows: one ground electrode 130 may be disposed to be opposite to the first discharge electrode 110 and the second discharge electrode 210, or the first ground electrode 130 and the second ground electrode 230 may be included, the first ground electrode 130 may be disposed to be opposite to the first discharge electrode 110, and the second ground electrode 230 may be disposed to be opposite to the second discharge electrode 210. Hereinafter, the description of the ground electrodes 130 embraces both of the above cases.

The description of the ground electrode 130 of the above-described first embodiment may be applied to the first and second ground electrodes 110 and 210 of this embodiment.

The housing 150 may be formed such that the circumferential surface 153 forming the opened first and second surfaces 151 and 152 is parallel to the flow path through which air flows. The housing 150 may be disposed on the air purifier 1, the air conditioner or the like to which the plasma sterilization modules 100 and 200 are applied, and may be disposed to be in contact with a surface forming the air flow path in the body of the air purifier 1 or the air conditioner. Therefore, the air introduced into the inlet port 12 may completely pass through the plasma sterilization modules 100 and 200, and then may flow to the outlet port 13.

Meanwhile, the intensity of the plasma discharge is determined depending on a distance between the discharge electrode 110 or 210 and the ground electrode 130, the diameter of the tip 114 or 214, and the level of applied voltage. The plasma sterilization module 100 or 200 in accordance with the second embodiment of the present disclosure may generate the plasma discharge of uniform intensity, because the distance between the first discharge electrode 110 and the ground electrode 130, the diameter of the tip 114, and the level of applied voltage remain the same in all areas where the plasma discharge occurs between the plurality of first discharge needles and the ground electrode 130.

The plasma discharge of uniform intensity may be generated even in the areas where the plasma discharge occurs between the plurality of second discharge needles 213 and the ground electrode 230. However, since the levels and polarities of the voltage applied to the first discharge electrode 110 and the second discharge electrode 210 may be different, the intensity of the plasma discharge occurring between the first discharge needle 113 and the ground electrode 130 may be different from the intensity of the plasma discharge occurring between the second discharge needle 213 and the ground electrode 230.

Figure 14:
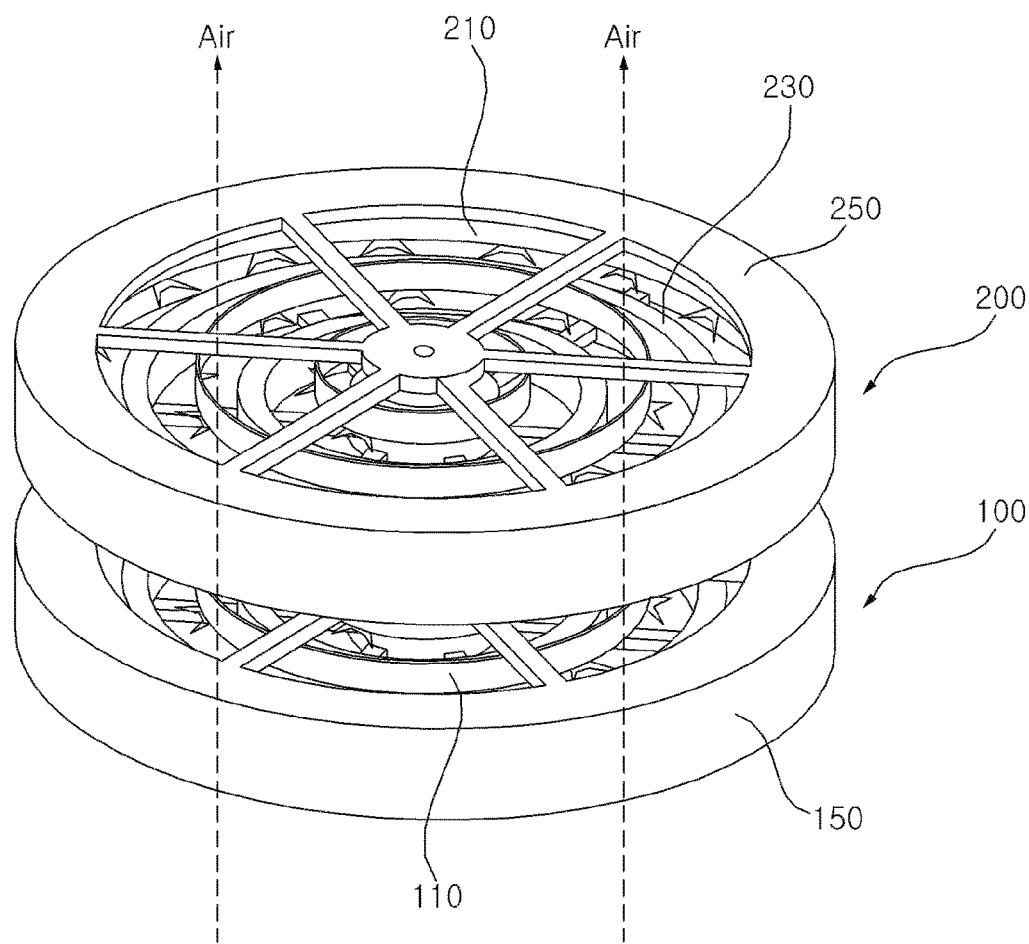
FIG. 14 is a perspective view illustrating the plasma sterilization module in accordance with the second embodiment of the present disclosure.
Figure 15:
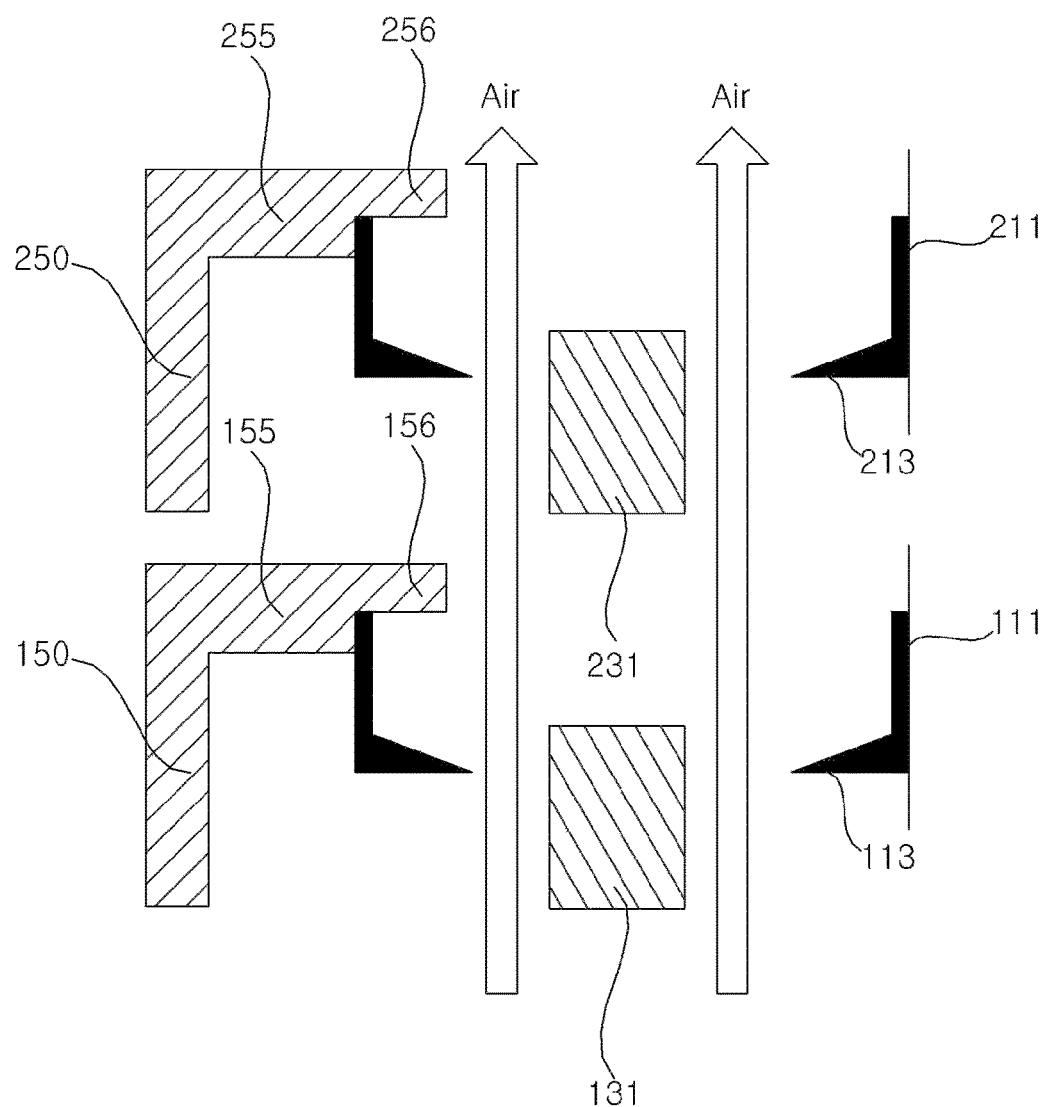
FIG. 15 is a conceptual view showing air which passes through a plasma discharge area occurring in a portion of the plasma sterilization module in accordance with the second embodiment of the present disclosure.
Figure 16:
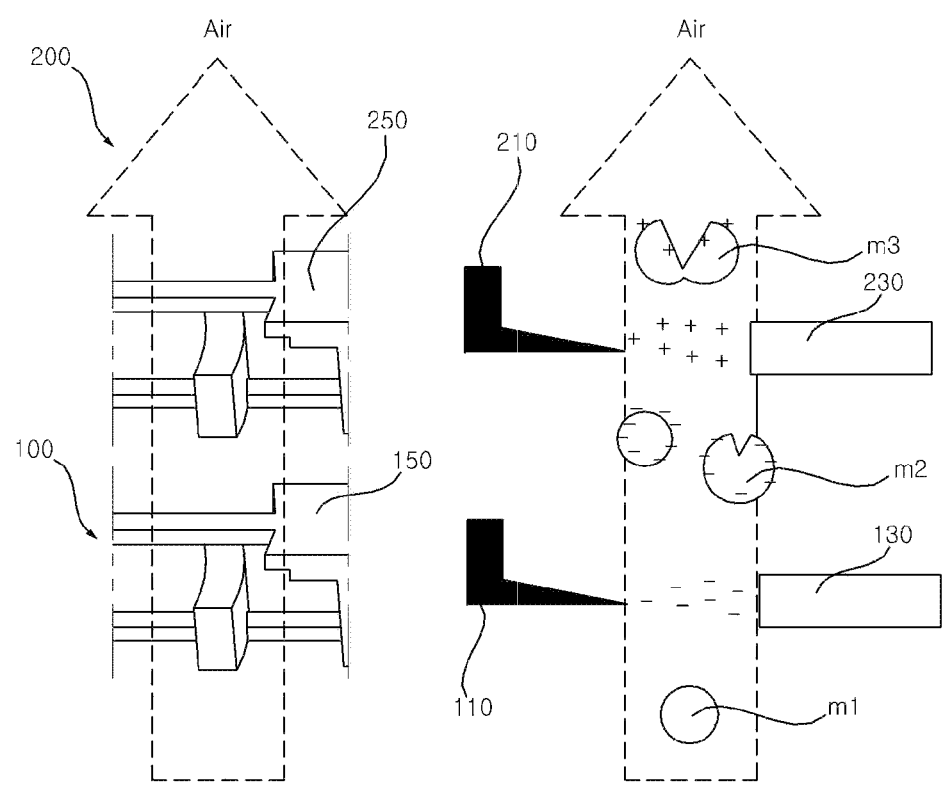
FIG. 16 is a conceptual view showing the sterilization principle of air which passes through the plasma discharge area of the plasma sterilization module in accordance with the second embodiment of the present disclosure.

Referring to FIGS. 14 to 16, the plasma sterilization modules 100 and 200 according to the second embodiment of the present disclosure include a first discharge module 100, and a second discharge module 200 which is disposed on the downstream of the air flow path compared to the first discharge module 100.

The first discharge module 100 include a first housing 150 which is disposed on a flow path through which air flows, and has a first surface 151 into which the air is introduced and a second surface 152 which is opposite to the first surface 151 and through which the introduced air is discharged towards the second discharge module 200, a first discharge electrode 110 which is disposed in the first housing 150, and a first ground electrode 130 which is disposed in the first housing 150 and is spaced apart from the first discharge electrode 110.

The second discharge module 200 include a second housing 250 which is disposed on a flow path through which air flows, and has a first surface 251 into which the air discharged from the first discharge module 100 is introduced and a second surface 252 which is opposite to the first surface 251 and through which the introduced air is discharged, a second discharge electrode 210 which is disposed in the second housing 250, and a second ground electrode 230 which is disposed in the second housing 250 and is spaced apart from the second discharge electrode 210.

The first discharge module 100 and the second discharge module 200 may be disposed to be parallel to each other, and be disposed such that the outlet port side of the first discharge module 100 and the inlet port side of the second discharge module 100 face each other. The first discharge module 100 and the second discharge module 200 may be disposed to be spaced apart from each other in the air flow direction, and be disposed such that the second surface 152 of the first housing 150 and the first surface 251 of the second housing 250 are opposite to each other.

The first discharge electrode 110 and the first ground electrode 130 may be disposed to be parallel to the circumferential surface 153 of the first housing, and the second discharge electrode 210 and the second ground electrode 230 may be disposed to be parallel to the circumferential surface 253 of the second housing.

The first discharge module 100 and the second discharge module 200 have the same configuration, and may have the same shape. However, different voltages may be applied to the first discharge module 100 and the second discharge module 200.

The ground electrodes 130 and 230 of the plasma sterilization module 10 according to the embodiment of the present disclosure include the first ground electrode 130 and the second ground electrode 230, and are disposed in the first housing 150 and the second housing 250, respectively.

The above description of the plasma sterilization module 100 according to the first embodiment may be applied to the first and second discharge modules 100 and 200 of this embodiment.

Hereinafter, matters which are common to the first discharge module 100 and the second discharge module 200 and are not unreasonable for interpretation will be collectively described as the discharge module 100 or 200. Likewise, the discharge electrodes 110 and 210, the ground electrodes 130 and 230, and the housings 150 and 250 are collectively described.

When it is described that the discharge electrodes 110 and 210 are disposed in the housings 150 and 250, this means that the first discharge electrode 110 is disposed in the first housing and the second discharge electrode 210 is disposed in the second housing. Furthermore, when it is described that the first and second discharge electrodes 110 and 210 may include the voltage application portions 118 and 218 to which a high voltage is applied, and the voltage application portions 118 and 218 may be seated on the hub rings 157 and 257 of the first and second housings 150 and 250, this is intended to clearly interpret a case where names of components included in the first discharge module and the second discharge module are distinguished by the expression "first and second" and a case where the names are not distinguished.

The first discharge module 100 of the plasma sterilization module 10 according to the first embodiment of the present disclosure includes the first housing 150, and the second discharge module 200 includes the second housing 250.

The housings 150 and 250 may be formed in the shape of a cylinder in which the first surfaces 151 and 251 and the second surfaces 152 and 252 are opened. The housings 150 and 250 may include rim surfaces 155 and 255 which protrude inwards from inner circumferential surfaces 153i and 253i (hereinafter, referred to as inner circumferences) and are located in either of the first surfaces 151 and 251 or the second surfaces 152 and 252, hub rings 157 and 257 located in the centers of either of the first surfaces 151 and 251 or the second surfaces 152 and 252, and radial spokes 158 and 258 connecting the rim surfaces 155 and 255 and the hub rings 157 and 257. Hereinafter, a case where the rim surfaces 155 and 255 and the hub rings 157 and 257 are located in the second surfaces 152 and 252 will be described as an example.

The housings 150 and 250 may have guide grooves 154 and 254 formed in the first surfaces 151 and 251 or the second surfaces 152 and 252 where the rim surfaces 155 and 255 are not located, the guide grooves being recessed outwards from the inner circumferences 153i and 253i. When the rim surfaces 155 and 255 are located in the second surfaces 152 and 252, the guide grooves 154 and 254 may be formed to be recessed outwards from ends of the inner circumferences 153i and 253i of the housings 150 and 250 in the proximity of the first surfaces 151 and 251.

The housings 150 and 250 may be formed such that the circumferential surfaces 153 and 253 forming the opened first surfaces 151 and 251 and the opened second surfaces 152 and 252 are parallel to the flow path through which air flows. Outer circumferential surfaces 153o and 253o (hereinafter, referred to as outer circumferences) of the housings 150 and 250 may be disposed to be in contact with a surface forming the air flow path in a body of an air purifier 1 or an air conditioner to which the plasma sterilization module 10 is applied.

When the inlet port 12 is disposed on the lower portion of the body of the air purifier 1 or the air conditioner to which the plasma sterilization modules 100 and 200 in accordance with the second embodiment of the present disclosure are applied, and the outlet port 13 is disposed on the upper portion of the body, the housings 150 and 250 may be disposed such that the first surfaces 151 and 251 face downwards and the second surfaces 152 and 252 face upwards.

The first discharge module 100 of the plasma sterilization modules 100 and 200 according to the second embodiment of the present disclosure includes the first discharge electrode 110, and the second discharge module 200 includes the second discharge electrode 210.

The discharge electrodes 110 and 210 may include a plurality of ring-shaped discharge electrode plates 111 and 211 which form concentric circles around the central axis of the housing 150. The number of the discharge electrode plates 111 and 211 may vary depending on the size of the housings 150 and 250. The first discharge electrode plates 111 is disposed to be parallel to the circumferential surface 153 of the first housing, and the second discharge electrode plate 211 is disposed to be parallel to the circumferential surface 253 of the second housing.

The first discharge electrode 110 includes a plurality of first discharge electrode plates 111 which are spaced apart from each other, and a plurality of first discharge needles 113 which are provided in each of the first discharge electrode plates 111 and generate a plasma discharge. The second discharge electrode 210 includes a plurality of second discharge electrode plates 211 which are spaced apart from each other, and a plurality of second discharge needles 213 which are provided in each of the second discharge electrode plates 211 and generate a plasma discharge.

The first and second discharge electrodes 110 and 210 may include voltage application portions 118 and 218 to which a high voltage is applied, and the voltage application portions 118 and 218 may be seated on the hub rings 157 and 257 of the first and second housings 150 and 250. The high voltage may be applied to the voltage application portions 118 and 218 through holes formed in the centers of the hub rings 157 and 257. Furthermore, the voltage application portions 118 and 218 may have holes which communicate with the holes formed in the centers of the hub rings 157 and 257.

The negative electrode of the power supply is connected to the voltage application portion 118 of the first discharge electrode 110, and the positive electrode of the power supply is connected to the voltage application portion 218 of the second discharge electrode 210, so that a high negative voltage is applied to the first discharge electrode 110 and a high positive voltage is applied to the second discharge electrode 210. A glow discharge may occur between the first discharge electrode 110 and the first ground electrode 130, and a streamer discharge may occur between the second discharge electrode 210 and the second ground electrode 230. In other words, the first discharge module 100 generates the glow discharge, while the second discharge module 200 generates the streamer discharge.

The first discharge module 100 of the plasma sterilization modules 10 according to the second embodiment of the present disclosure includes the first ground electrode 130, and the second discharge module 200 includes the second ground electrode. The first ground electrode 130 may be disposed to be opposite to the first discharge electrode 110, and the second ground electrode 230 may be disposed on a downstream side compared to the first ground electrode 130, and be disposed to be opposite to the second discharge electrode 210.

The ground electrodes 130 and 230 include counter electrode plates 131 and 231, and the counter electrode plates 131 and 231 are disposed to be opposite to the discharge electrodes 110 and 210. The first ground electrode 130 may include first counter electrode plates 131 disposed between the plurality of first discharge electrode plates 111 which are spaced apart from each other, and ground-electrode support portions 136 which connect the plurality of first counter electrode plates 131 to each other. Furthermore, the second ground electrode 230 may include second counter electrode plates 231 disposed between the plurality of second discharge electrode plates 211 which are spaced apart from each other, and ground-electrode support portions 236 which connect the plurality of second counter electrode plates 231 to each other.

The counter electrode plates 131 and 231 may form concentric circles around the central axes of the housings 150 and 250 together with the discharge electrode plates 111 and 211. The first counter electrode plate 131 may be disposed to be parallel to the circumferential surface 153 of the first housing, and the second counter electrode plate 231 may be disposed to be parallel to the circumferential surface 253 of the second housing.

The counter electrode plates 131 and 231 may be disposed in centers between the plurality of discharge electrode plates 111 and 211 which are spaced apart from each other. The distances between the plurality of first discharge needles 113 and the first counter electrode plates 131 may be uniform. The distances between the plurality of second discharge needles 213 and the second counter electrode plates 231 may be uniform. The distances between the first discharge needles 113 and the first counter electrode plates 131 need not the same as the distances between the second discharge needles 213 and the second counter electrode plates 231.

FIG. 16 is a conceptual view showing the sterilization principle of air which passes through the plasma discharge area of the plasma sterilization module in accordance with the second embodiment of the present disclosure.

In the plasma sterilization modules 100 and 200 according to the second embodiment of the present disclosure, the first discharge module 100 may be supplied with a negative voltage to generate a glow discharge, and the second discharge module 200 may be supplied with a positive voltage to generate a streamer discharge.

The high negative voltage may be applied to the first discharge electrode 110 of the first discharge module 100 to generate the glow discharge towards the first ground electrode 130. The positive voltage may be applied to the second discharge electrode 210 of the second discharge module 200 to generate the streamer discharge towards the second ground electrode 230. The streamer discharge which may occur when the positive voltage is applied to the discharge electrode 210 causes an electron avalanche when more electric energy is applied in the glow discharge, forms a discharge area wider than that of the glow discharge, and is advantageous for sterilization treatment.

While airborne microbes m1 introduced into the first discharge module 100 pass through the glow discharge area between the first discharge electrode 110 and the first ground electrode 130, negative charges are accumulated in cell walls. The metabolism of microbes m2 in which the negative charges are accumulated may become impossible because the tension of the cell walls is broken by the Coulomb force of the charges and the cell walls are torn. Thus, the air may be primarily sterilized.

The amount of the charges generated by the glow discharge when the high negative voltage is applied may be less than that of the charges generated by the streamer discharge. Therefore, the microbes m2 which have passed through the first discharge module 100 may accumulate negative charges, but surviving microbes m2 may exist. The airborne microbes m2 which survive after passing through the first discharge module 100 pass through the second discharge module 200.

The microbes m2 introduced into the second discharge module 200 pass through the streamer discharge area between the second discharge electrode 210 and the second ground electrode 230, and a potential difference is maximized. Thus, the metabolism of microbes m3 which have passed through the second discharge module 200 becomes impossible because the tension of the cell walls is broken by the Coulomb force of the charges and the cell walls are torn. As a result, the air may be secondarily sterilized, so that sterilization performance can be greatly improved.

In order to measure the sterilization performance of the plasma sterilization modules 100 and 200 according to the second embodiment of the present disclosure, air flows through the plasma sterilization modules 100 and 200 at a flow rate of 1 m/s, and the concentration of microbes m1 present in an upstream area before the air passing through the plasma sterilization modules 100 and 200 is compared with the concentration of microbes m3 present in a downstream area after the air passing through the plasma sterilization modules 100 and 200. One-pass sterilization performance measured as such is experimentally observed to be 80% or more.

Therefore, the plasma sterilization module 100 according to the second embodiment of the present disclosure can realize improved sterilization performance compared to the sterilization module using only the streamer discharge as well as the sterilization module using the ultraviolet rays.

If the plasma sterilization module 100 according to the second embodiment of the present disclosure is applied, ozone may be generated at a level below a standard concentration.

The plasma sterilization module 10 is disposed on the flow path through which air flows, in the body of the air purifier 1, the first discharge electrode 110 is connected to the negative electrode of the power supply to generate the glow discharge towards the first ground electrode, and the second discharge electrode 210 is connected to the positive electrode of the power supply to generate the plasma discharge towards the second ground electrode 230. By applying the high negative voltage of about 3.5 kV to the first discharge electrode 110 and applying the high positive voltage of about 3.5 kV to the second discharge electrode 210, the plasma discharge may be generated. The plasma sterilization module 10 is configured such that the first surface 151 which is the upstream side of the flow path through which the air flows, and the second surface 152 which is the downstream side are opened, so that the air directly passes through the plasma discharge area to be sterilized.

Figure 17:
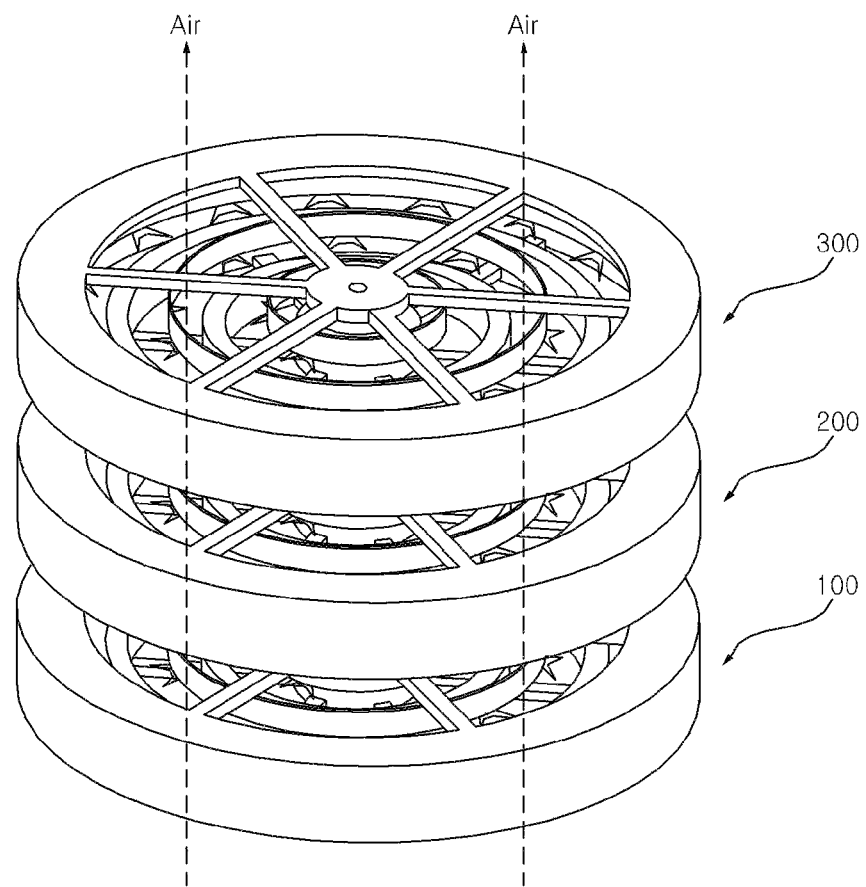
FIG. 17 is a perspective view illustrating a plasma sterilization module in accordance with a third embodiment of the present disclosure.

FIG. 17 is a perspective view illustrating a plasma sterilization module in accordance with a third embodiment of the present disclosure.

The plasma sterilization modules 100, 200, and 300 according to the third embodiment of the present disclosure include a plurality of discharge modules 100, 200, and 300.

The plurality of discharge modules 100, 200, and 300 include housings 150, 250, and 350, discharge electrodes 210, 210, and 310, and ground electrodes 130, 230, and 330.

Figure 12:
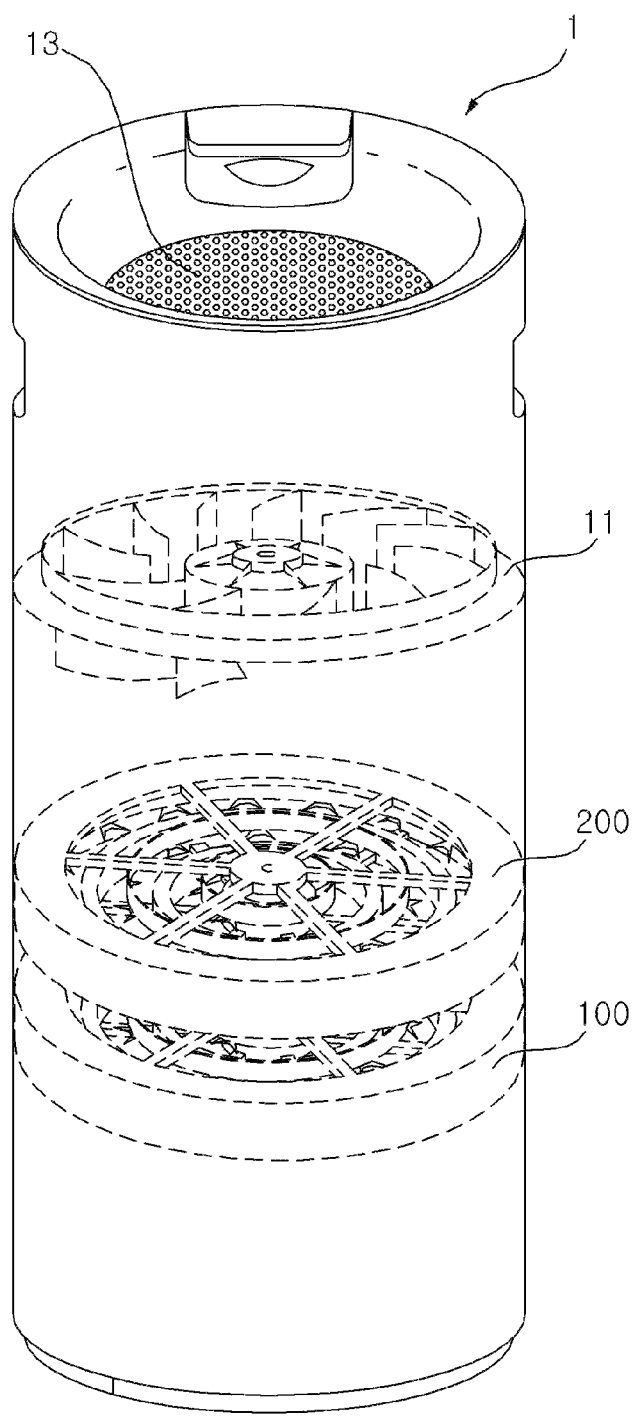
FIG. 12 is a front view of an air purifier having a plasma sterilization module in accordance with a second embodiment of the present disclosure.
Figure 13:
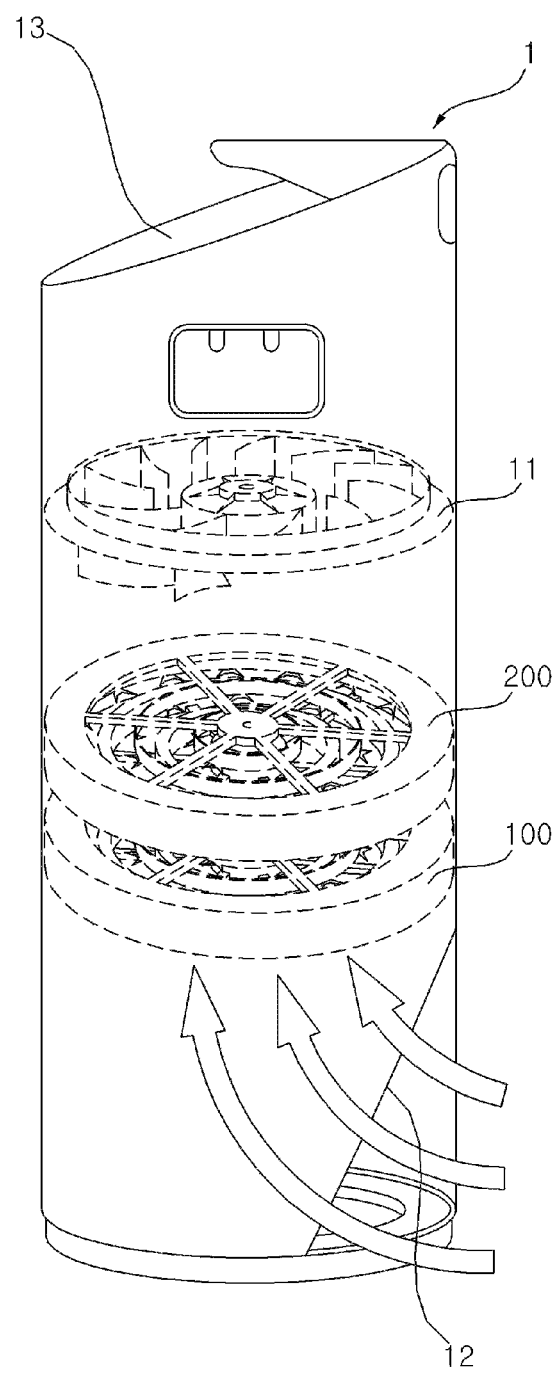
FIG. 13 is a side view of the air purifier illustrated in FIG. 12.

In other words, the plasma sterilization module 10 according to the second embodiment of the present disclosure includes the above-described first and second discharge modules 100 and 200, and further includes a third discharge module. Although FIG. 12 shows three discharge modules, three or more discharge modules may be included.

The discharge electrodes 110, 210, and 310 may include the first discharge electrode 110, the second discharge electrode 210 disposed on the downstream side of the air flow path compared to the first discharge electrode 110, and the third discharge electrode disposed on the downstream side of the air flow path compared to the second discharge electrode 210.

The ground electrodes 130, 230, and 330 may include the first ground electrode 130 disposed to be opposite to the first discharge electrode 110, the second ground electrode 230 disposed to be opposite to the second discharge electrode 210, and the third ground electrode 330 disposed to be opposite to the third discharge electrode 310.

The third discharge electrode 310 may be supplied with a high positive voltage to generate a streamer discharge towards the third ground electrode 300.

The first discharge module 100 may include the first discharge electrode 110 and the first ground electrode 130, the second discharge module 200 may include the second discharge electrode 210 and the second ground electrode 230, and the third discharge module 300 may include the third discharge electrode 310 and the third ground electrode 330.

The plurality of discharge modules 100, 200, and 300 may be disposed to be parallel to each other on the flow path through which the air flows, and may be disposed such that the second surface of the discharge module disposed on the upstream side is opposite to the first surface of the discharge module disposed on the downstream side. Therefore, the discharge modules may be disposed such that the second surface 152 of the first discharge module 100 and the first surface 251 of the second discharge module 200 are opposite to each other and the second surface 252 of the second discharge module 200 and the first surface 351 of the third discharge module 300 are opposite to each other.

The plurality of discharge modules 100, 200, and 300 may be disposed to be spaced apart from each other in the air flow direction.

The plurality of discharge modules 100, 200, and 300 may include a glow discharge module 100 and streamer discharge modules 200 and 300, and may include two or more streamer discharge modules 200 and 300. A high negative voltage may be applied to the first discharge module 100 to generate the glow discharge, and a high positive voltage may be applied to the second and third discharge modules 200 and 300 to generate the streamer discharge.

The first discharge module 100 applies the negative voltage to the discharge electrode 110 to generate the glow discharge. The ground electrode 130 provides a ground to the first discharge module, and causes the glow discharge occurring in the discharge electrode 110 to be generated towards the ground electrode 130.

Airborne microbes m are sterilized while passing through the second discharge module 200, and then surviving microbes are sterilized while passing through the third discharge module 300, so that it is possible to provide sterilization performance higher than that of the plasma sterilization module according to the first embodiment.

The ground electrodes 130, 230, and 330 may be connected to a ground electrode of a commercial power supply or may be connected to a control circuit board of the air purifier 1 or the like, thus providing a ground to the plasma sterilization module 10, and causing the plasma discharge occurring in the discharge electrodes 110, 210, and 310 to be generated towards the ground electrodes 130, 230, and 330.

Since other components and operations are equal or similar to those of the first and second embodiments of the present disclosure, the same reference numerals are used and a detailed description thereof will be omitted.

Figure 18:
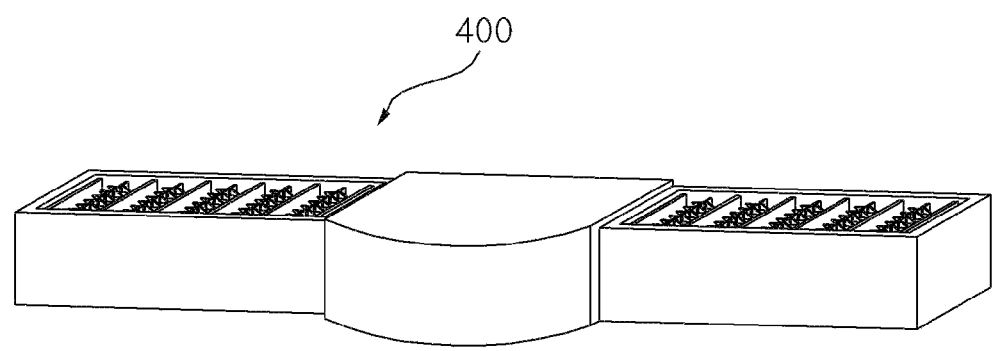
FIG. 18 is a perspective view illustrating a plasma sterilization module in accordance with a fourth embodiment of the present disclosure.
Figure 21:
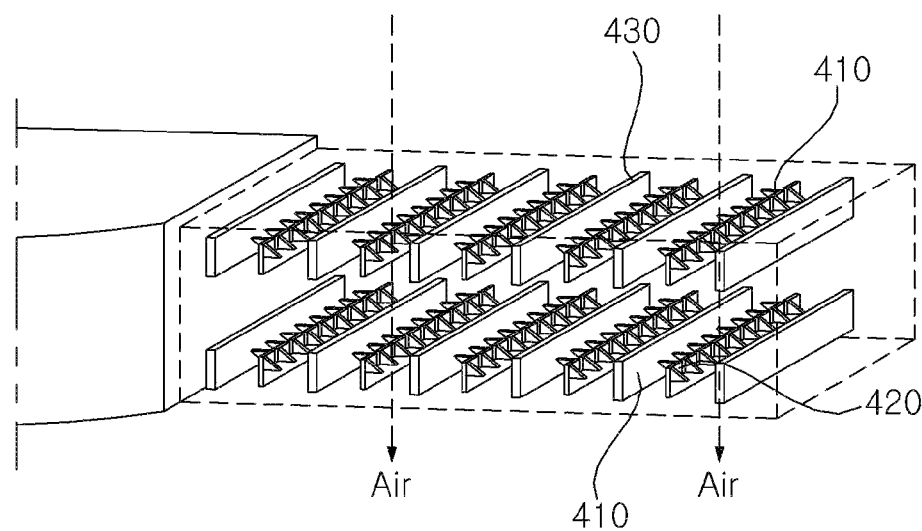
FIG. 21 is a conceptual view showing the interior of a housing of the plasma sterilization module in accordance with the fourth embodiment of the present disclosure.

FIGS. 18 and 21 are diagrams illustrating a plasma sterilization module in accordance with a fourth embodiment of the present disclosure.

The plasma sterilization module 400 in accordance with the fourth embodiment of the present disclosure may accommodate a plurality of first discharge electrodes 410, a plurality of second discharge electrodes 420, and a ground electrode 430 in one housing 450.

The first discharge electrode 410 may be disposed on the upstream side of the air flow path, while the second discharge electrode 420 may be disposed on the downstream side compared to the first discharge electrode 410.

Figure 19:
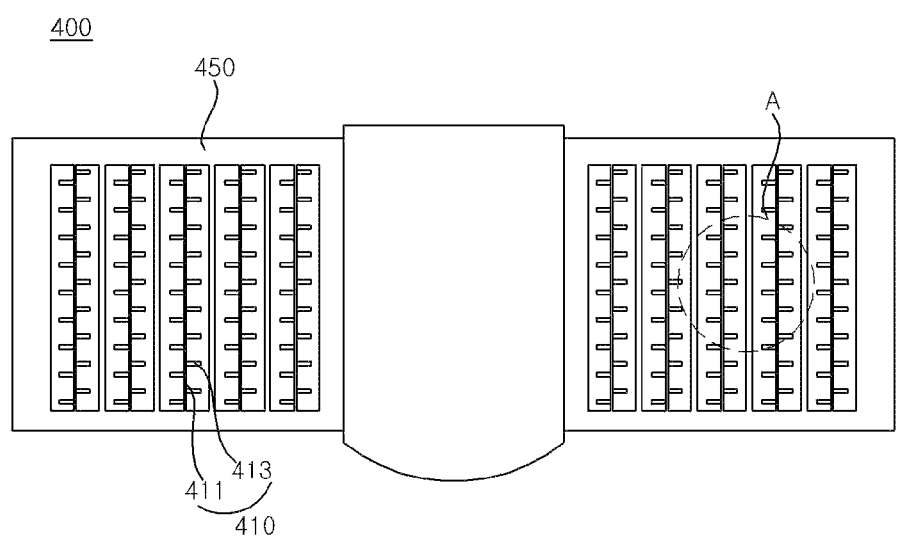
FIG. 19 is a plan view of the plasma sterilization module in accordance with the fourth embodiment of the present disclosure.

As shown in FIG. 19, the ground electrodes 430 and 440 may include a first ground electrode 430 disposed to be opposite to the first discharge electrode 410, and a second ground electrode 440 disposed to be opposite to the second discharge electrode 420. Alternatively, unlike FIG. 19, the ground electrode 430 may be formed long in the air flow direction to be opposite to the first discharge electrode 410 and the second discharge electrode 420. Hereinafter, as shown in FIG. 19, an example where the ground electrodes 430 and 440 include the first and second ground electrodes 430 and 440 will be described.

The housing 450 may have a cylindrical shape as in the first, second, and third embodiments, or may be shaped such that the circumferential surface 453 has a polygonal section, as shown in FIG. 19. The cylindrical housing 450 has been described in the first and second embodiments. Hereinafter, an example where the circumferential surface 453 has the polygonal section will be described.

The discharge electrodes 410 and 420 may include discharge electrode plates 411 and 421 disposed to be parallel to any one portion of the circumferential surface 453, and discharge needles 413 and 423 provided on the discharge electrode plates.

The ground electrodes 430 and 440 may have counter electrode plates 431 and 441 disposed to be parallel to the discharge electrode plates 411 and 421.

As shown in FIG. 19, the housing 450 may be shaped such that the circumferential surface 453 has a rectangular section, and the discharge electrode plate 411 and the counter electrode plate 431 may be disposed to be parallel to a pair of facing portions of the circumferential surface 453 of the housing 450.

Figure 20:
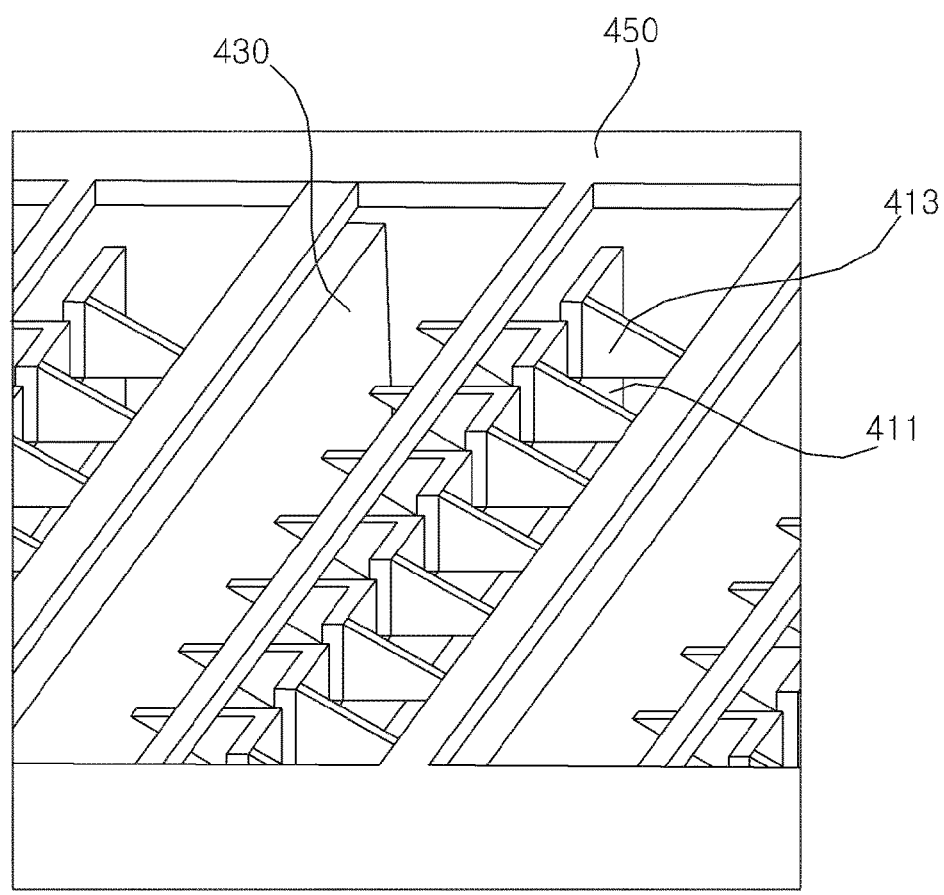
FIG. 20 is an enlarged view of area A shown in FIG. 19.

As shown in FIG. 20, the first discharge needle 413 may have two tips 414 which are symmetrical to each other, and the second discharge needle 423 may have two tips 424 which are symmetrical to each other. The discharge needles 413 and 423 may be made in the shape of a parallel trapezoidal, and may be bent such that the tips 414 and 424 protrude towards the ground electrodes 430 and 440. Any one of the two tips 414 provided on the first discharge needle 413 may be bent towards an inner ground electrode 430, while the other may be bent towards an outer ground electrode 430. Further, any one of the two tips 424 provided on the second discharge needle 423 may be bent towards an inner ground electrode 440, while the other may be bent towards an outer ground electrode 440.

A plurality of plasma sterilization modules 400 according to the fourth embodiment of the present disclosure may be disposed on the air conditioner 3 or the like, and may be provided in a direction perpendicular to the air flow path, and the circumferential surfaces 453 may be in contact with each other to allow air introduced into the air conditioner 3 or the like to completely pass through the plasma sterilization module 400.

A negative voltage may be applied to the first discharge electrode 410 to generate a glow discharge, while a positive voltage may be applied to the second discharge electrode 420 to generate the streamer discharge.

Since other components and operations are equal or similar to those of the first and second embodiments of the present disclosure, the same reference numerals are used and a detailed description thereof will be omitted.

The plasma sterilization module according to the embodiment of the present disclosure may be applied to the air purifier 1, as shown in FIGS. 1, 2, 12, and 13.

Figure 22A:
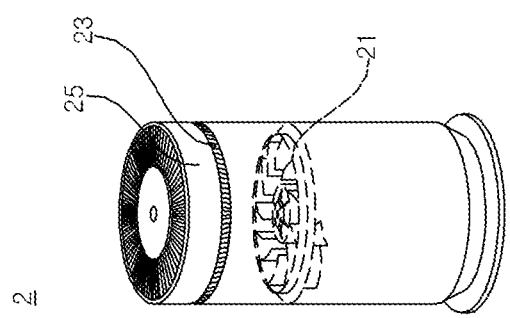
FIGS. 22A and 22B illustrate a perspective view of an air purifier having a flow change device and a plasma sterilization module in accordance with an embodiment of the present disclosure, and a sectional view of the flow change device.
Figure 22B:
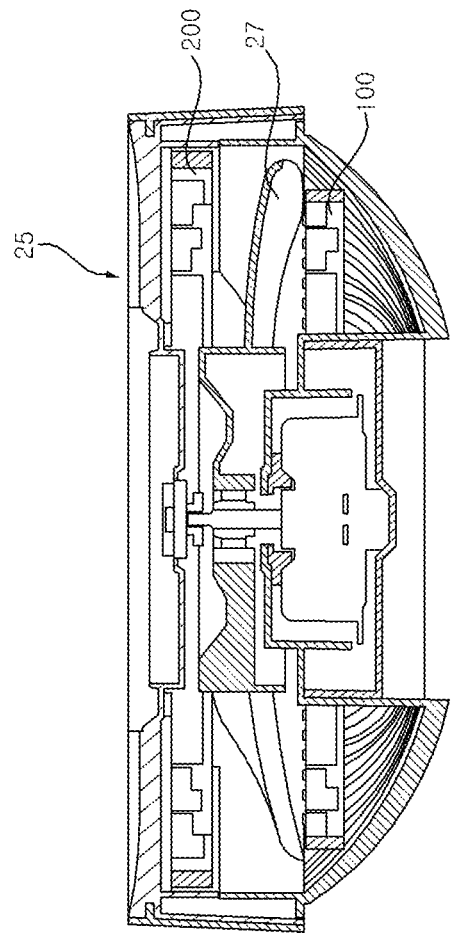
Figure 23:
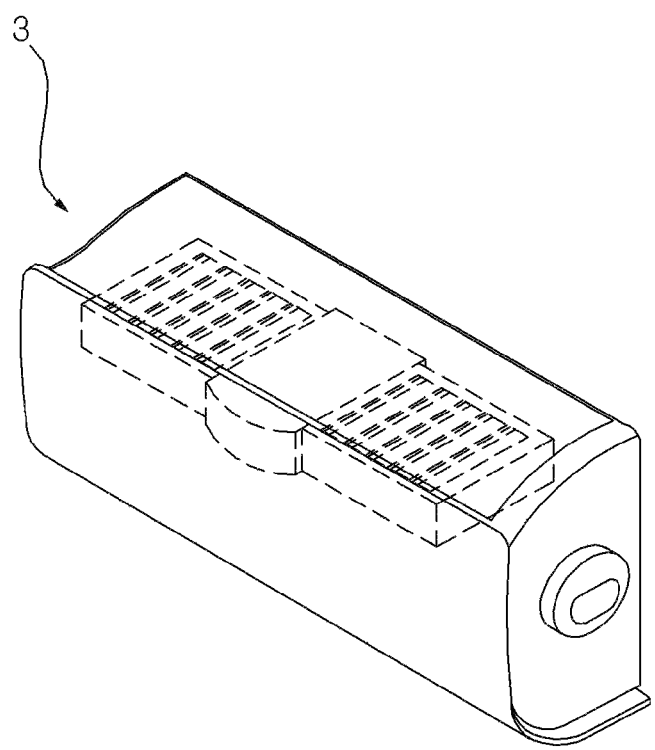
FIG. 23 is a conceptual view illustrating an air conditioner having a plasma sterilization module in accordance with an embodiment of the present disclosure.

As shown in FIG. 22, the air purifier 2 may include a main fan 21 which generates an air flow, a discharge guide device 23 which discharges air passing through the main fan 21 and has a discharge grill which is concave downwards, and a flow change device 25 which is movably provided to adjust the flow direction of the air discharged from the discharge grill. The flow change device 25 may include a flow change fan 27.

When the plasma sterilization module 100 according to the embodiment of the present disclosure is applied to the air purifier 2 having the flow change device 25, the plasma sterilization module 100 may be provided in the body, or may be disposed in the flow change device 25.

When the plasma sterilization module 100 is provided in the flow change device 25, the first discharge module 100 may be disposed on an upstream side compared to the flow change fan 27, and the second discharge module 200 may be disposed on a downstream side compared to the flow change fan 27.

As shown in FIG. 21, the plasma sterilization module 400 according to the embodiment of the present disclosure may be applied to the air conditioner 3 having the heat exchanger.

The plasma sterilization module 400 may be disposed on the inlet side of the air conditioner, the heat exchanger may be disposed on a downstream side compared to the plasma sterilization module 400, and the blower fan may be disposed on an outlet side. Since the plasma sterilization module is disposed on an upstream side compared to the heat exchanger and the sterilized air passes through the heat exchanger, the growth of bacteria in the heat exchanger can be prevented.

Although preferred embodiments of the present disclosure have been shown and described, it is obvious to those skilled in the art that the present disclosure is not limited to the above-described embodiments, and various modifications may be made without departing from the spirit of the appended claims. These modifications should be construed as falling within the technical spirit or scope of the present disclosure.

What is claimed is:

1. A plasma sterilization module, comprising:
a housing disposed on a flow path through which air flows, and having a first surface into which the air is introduced and a second surface which is opposite to the first surface and through which the introduced air is discharged;
a discharge electrode disposed in the housing, the discharge electrode including:
a first discharge electrode, and
a second discharge electrode disposed downstream of the air flow path compared to the first discharge electrode; and
a ground electrode disposed in the housing and spaced apart from the first and second discharge electrodes,
wherein the first discharge electrode is supplied with a negative voltage to generate a glow discharge towards the ground electrode,
wherein the second discharge electrode is supplied with a positive voltage to generate a streamer discharge towards the ground electrode, and
wherein the discharge electrode comprises:
a plurality of discharge electrode plates spaced apart from each other; and
a plurality of discharge needles provided on the plurality of discharge electrode plates, respectively, to generate a plasma discharge,
wherein the ground electrode comprises a counter electrode plate disposed between the plurality of discharge electrode plates which are spaced apart from each other.

2. The plasma sterilization module of claim 1, wherein the discharge electrode plates and the counter electrode plate are disposed to be parallel to a circumferential surface of the housing forming the first and second surfaces.

3. The plasma sterilization module of claim 1, wherein the discharge needles are provided with two tips which are symmetrical to each other.

4. The plasma sterilization module of claim 1, wherein the ground electrode comprises a plurality of counter electrode plates.

5. The plasma sterilization module of claim 4,
wherein the discharge electrode comprises a discharge-electrode support portion which connects the plurality of discharge electrode plates to each other and is disposed to be supported on the housing, and
wherein the ground electrode comprises a ground-electrode support portion which is connected to the counter electrode plate and is disposed to be supported on the housing.

6. The plasma sterilization module of claim 4, wherein the plurality of discharge electrode plates and the plurality of counter electrode plates are disposed to have the same distance between the discharge electrode plate and the counter electrode plate which are adjacent to each other.

7. The plasma sterilization module of claim 4, wherein the plurality of discharge needles located between the plurality of counter electrode plates include:
a first discharge needle protrudes towards a first counter electrode plate which is disposed inside the discharge electrode plate that has the first discharge needle and a second discharge needle; and
the second discharge needle protrudes towards a second counter electrode plate which is disposed outside the discharge electrode plate.

8. The plasma sterilization module of claim 1,
wherein the housing is formed to have a shape of a cylinder with the first and second surfaces that are opened,
wherein the plurality of discharge electrode plates have ring shapes forming concentric circles around a central axis of the housing, and wherein the ground electrode comprises a plurality of ring-shaped counter electrode plates forming concentric circles around the central axis of the housing.

9. The plasma sterilization module of claim 1,
wherein the discharge electrode further includes a third discharge electrode disposed downstream of the air flow path compared to the second discharge electrode, and
wherein the third discharge electrode is supplied with a positive voltage to generate a streamer discharge towards the ground electrode.

10. The plasma sterilization module of claim 1,
wherein the ground electrode comprises:
  a first ground electrode disposed opposite to the first discharge electrode; and
  a second ground electrode disposed downstream of the air flow path compared to the first ground electrode, and disposed opposite to the second discharge electrode,
wherein the housing comprises:
  a first housing configured to accommodate the first discharge electrode and the first ground electrode; and
  a second housing configured to accommodate the second discharge electrode and the second ground electrode, and
wherein the plasma sterilization module comprises:
  a first discharge module having the first discharge electrode, the first ground electrode, and the first housing; and
  a second discharge module having the second discharge electrode, the second ground electrode, and the second housing, and disposed downstream of the air flow path compared to the first discharge module.

11. The plasma sterilization module of claim 10, wherein the first discharge module and the second discharge module are formed to have the same shape.

12. The plasma sterilization module of claim 10, wherein the first discharge module and the second discharge module are disposed such that they are spaced apart from each other in the direction where the air flows.

13. The plasma sterilization module of claim 1, wherein the discharge electrode and the ground electrode are disposed so as to allow air introduced into the first surface to pass through an area in which a plasma discharge occurs, and be discharged to the second surface.

14. The plasma sterilization module of claim 13, wherein the discharge electrode and the ground electrode are disposed such that the area in which the plasma discharge occurs intersects with the flow path of the air.

15. The plasma sterilization module of claim 14, wherein the discharge electrode and the ground electrode are disposed such that the area in which the plasma discharge occurs is perpendicular to a direction in which the air flows.

16. The plasma sterilization module of claim 13, wherein a circumferential surface of the housing extends parallel to the flow path through which the air flows.

17. The plasma sterilization module of claim 16, wherein the discharge electrode and the ground electrode are disposed to be parallel to the circumferential surface of the housing.

* * * * *